(12) United States Patent
Nishiyama et al.

(10) Patent No.: US 7,482,490 B2
(45) Date of Patent: Jan. 27, 2009

(54) AMINE COMPOUND HAVING FLUORENE GROUP AS FRAMEWORK, PROCESS FOR PRODUCING THE AMINE COMPOUND, AND USE OF THE AMINE COMPOUND

(75) Inventors: Masakazu Nishiyama, Yamaguchi (JP); Naoki Matsumoto, Yamaguchi (JP); Hisao Eguchi, Yamaguchi (JP)

(73) Assignee: Tosoh Corporation, Shunan-shi (JP)

( * ) Notice: Subject to any disclaimer, the term of this patent is extended or adjusted under 35 U.S.C. 154(b) by 266 days.

(21) Appl. No.: 10/585,945

(22) PCT Filed: Jan. 14, 2005

(86) PCT No.: PCT/JP2005/000727

§ 371 (c)(1),
(2), (4) Date: Jul. 11, 2006

(87) PCT Pub. No.: WO2005/068413

PCT Pub. Date: Jul. 28, 2005

(65) Prior Publication Data

US 2008/0194878 A1 Aug. 14, 2008

(51) Int. Cl.
*C07C 211/00* (2006.01)
*C07D 285/00* (2006.01)
*C07D 209/00* (2006.01)
*C07D 409/00* (2006.01)
*C07D 233/00* (2006.01)

(52) U.S. Cl. .................. 564/308; 548/126; 548/445; 549/59; 549/68; 428/917

(58) Field of Classification Search .................. None
See application file for complete search history.

(56) References Cited

U.S. PATENT DOCUMENTS

2004/0110958 A1 6/2004 Nishiyama et al.
2006/0186797 A1 8/2006 Nishiyama et al.

FOREIGN PATENT DOCUMENTS

DE 101 09 463 A1 10/2002
EP 1 400 578 3/2004
JP 10 95972 4/1998

OTHER PUBLICATIONS

Tsutomu, et al. "Diphenylfluorene Derivitives and Organic Electroluminescence Devices Using Them With High Luminescence Efficiency", Database accession No. 139:252299, abstract, JP 2003-261472, Mitsui Chemicals, XP-002423536, Sep. 16, 2003, pp. 1-5.
U.S. Appl. No. 10/585,945, filed Jul. 11, 2006, Nishiyama et al.

*Primary Examiner*—Brian J Davis
(74) *Attorney, Agent, or Firm*—Oblon, Spivak, McClelland, Maier & Neustadt, P.C.

(57) ABSTRACT

Novel amine compounds that can be utilized as hole transport materials, hole injection materials or the like of organic electroluminescence devices, electrophotographic receptors or the like, and their production processes are provided.

The novel amine compound is represented by the following general formula (1).

In the formula, $R^1$ and $R^2$ each independently represents hydrogen atom, a linear, branched or cyclic alkyl group or alkoxy group, an aryl group, an aryloxy group or a halogen atom; $Ar^1$ and $Ar^2$ each independently represents a substituted or unsubstituted aryl group or heteroaryl group, and may form a nitrogen-containing heterocyclic ring together with the nitrogen atom bonded thereto; and $Ar^3$ each independently represents a substituted or unsubstituted phenyl group, naphthyl group, biphenylyl group, terphenylyl group, anthryl group, fluorenyl group or pyridyl group (except for amino-substituted groups); and M represents a single bond, an arylene group or a heteroarylene group.

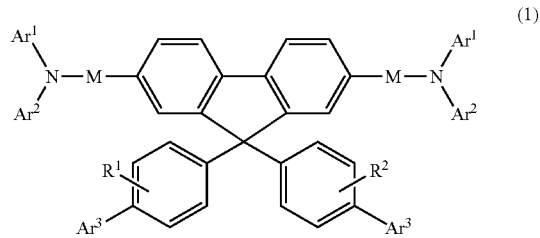

(1)

14 Claims, 4 Drawing Sheets

AMINE COMPOUND HAVING FLUORENE GROUP AS FRAMEWORK, PROCESS FOR PRODUCING THE AMINE COMPOUND, AND USE OF THE AMINE COMPOUND

TECHNICAL FIELD

The present invention relates to an amine compound having a fluorene group as a mother nucleus, a process for producing the amine compound, and an organic electroluminescence (EL) device using the amine compound. The amine compound having a fluorene group as a mother nucleus can be used as photosensitive materials and organic photoconductive materials, and more specifically, can be utilized as hole transport or hole injection materials and luminescent materials of organic EL devices used for planar light sources or displays, electrophotographic receptors, etc.

BACKGROUND ART

Organic photoconductive materials that are developed as photosensitive materials or hole transport materials have many advantages such as low costs, variable processability, and non-pollution, and many compounds are proposed. For example, there are disclosed materials such as oxadiazole derivatives (for example, see Patent Document 1), oxazole derivatives (for example, see Patent Document 2), hydrazone derivatives (for example, see Patent Document 3), tri-arylpyrazoline derivatives (for example, see Patent Documents 4 and 5), arylamine derivatives (for example, see Patent Documents 6 and 7), and stilbene derivatives (for example, see Patent Documents 8 and 9).

Above all, arylamine derivatives such as 4,4',4"-tris[N,N-(1-naphthyl)phenylamino]triphenylamine (1-TNATA), 4,4',4"-tris[N,N-(m-tolyl)phenylamino]triphenylamine (MT-DATA), 4,4'-bis[N-(1-naphthyl)-N-phenylamino]biphenyl (α-NPD), and 4,4'-bis[N-(m-tolyl)-N-phenylamino]biphenyl (TPD) are largely used as hole transport or hole injection materials (for example, see Non-Patent Documents 1 and 2).

Recently, many fluorene derivatives are developed (for example, see Patent Documents 10, 11, 12, 13, 14 and 16).

However, those materials have drawbacks such as poor stability and poor durability. For example, because a-NPD is originally a crystalline compound, a-NPD thin film formed by vacuum deposition causes crystallization or cohesion when it is allowed to stand for about 2 weeks. As a result, the thin film becomes white turbid. Further, 2,7-bis(dinaphthylamino)-9,9-dimethylfluorene in which 9,9-positions are dimethyl groups (for example, see Patent Document 11) and 2,7-bis(N,N-diphenylamino)-9,9-diphenylfluorene in which 9,9-positions are diphenyl groups (for example, see Patent Document 16), that are representative fluorene derivatives, also have high crystallinity, and therefore have the same problems as above. As a result, in the case of utilizing to organic thin film devices such as organic EL devices, there is the problem that the possibility of causing short, dark spot or the like is large. At present, development of hole transport materials having an excellent hole transport capability, an excellent thin film stability and high Tg (glass transition temperature) is desired. Further, as a process of producing arylamines, there is known a method of using a catalyst comprising trialkylphosphines and a palladium compound in the amination reaction of aryl halides by an amine compound in the presence of a base (for example, see Patent Document 15).

Patent Document 1
   U.S. Pat. No. 3,189,447 (Claims)
Patent Document 2
   U.S. Pat. No. 3,257,203 (Claims)
Patent Document 3
   JP-A-54-59143 (Claims)
Patent Document 4
   JP-A-51-93224 (Claims)
Patent Document 5
   JP-A-55-108667 (Claims)
Patent Document 6
   JP-A-55-144250 (Claims)
Patent Document 7
   JP-A-56-119132 (Claims)
Patent Document 8
   JP-A-58-190953 (Claims)
Patent Document 9
   JP-A-59-195658 (Claims)
Patent Document 10
   JP-A-11-35532 (Claims)
Patent Document 11
   JP-A-12-16973 (Claims)
Patent Document 12
   JP-A-12-302756 (Claims)
Patent Document 13
   JP-A-12-327638 (Claims)
Patent Document 14
   JP-A-13-39933 (Claims)
Patent Document 15
   JP-A-10-139742 (Claims)
Patent Document 16
   JP-A-10-95972 (Claims)
Non-Patent Document 1
   *Advanced Materials*, (Germany), 1998, Vol. 10, No. 14, pp. 1108-1112 (FIG. 1 and Table 1)
Non-Patent Document 2
   *Journal of Luminescence*, (Holland), 1997, 72-74, pp. 985-991 (FIG. 1)

DISCLOSURE OF THE INVENTION

An object of the present invention is to provide novel materials having excellent hole transport capability, excellent thin film stability, and durability of having Tg higher than that of α-NPD or MTDATA. More particularly, the present invention provides a novel amine compound suitable for hole transport materials and luminescent materials of organic EL devices, etc.

Another object of the present invention is to provide a process of producing such a novel amine compound.

Still another object of the present invention is to provide an organic electroluminescence device using such a novel amine compound.

As a result of extensive and intensive investigations, the present inventors have found that an amine compound represented by the following general formula (1) has high Tg, many compounds of those are not crystalline compound, and have an amorphous structure, thereby having excellent thin film stability, and even if showing crystallinity, the thin film does not become white turbid over a long period of time, which is considered due to a caldo structure ("caldo" is a term which means a hinge, and shows a structure that cyclic groups directly bond to a main chain), and have completed the present invention.

The present invention relates to an amine compound having fluorene as a mother nucleus, represented by the general formula (1):

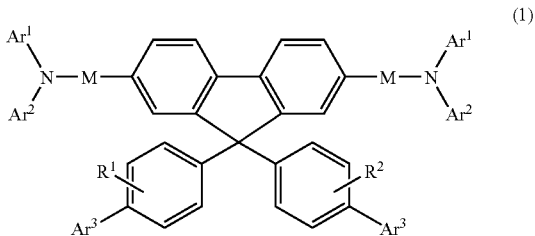

(1)

wherein $R^1$ and $R^2$ each independently represents hydrogen atom, a linear, branched or cyclic alkyl group or alkoxy group, an aryl group, an aryloxy group or a halogen atom; $Ar^1$ and $Ar^2$ each independently represents a substituted or unsubstituted aryl group or heteroaryl group, and may form a nitrogen-containing heterocyclic ring together with the nitrogen atom bonded thereto; $Ar^3$ each independently represents a substituted or unsubstituted phenyl group, naphthyl group, biphenylyl group, terphenylyl group, anthryl group, fluorenyl group or pyridyl group (except for amino-substituted groups); and M represents a single bond, arylene group or heteroarylene group.

The present invention further relates to a process for producing the amine compound, which comprises reacting fluorene derivatives represented by the following general formula (4) and arylboronic acid represented by the following general formula (5) in the presence of a palladium catalyst.

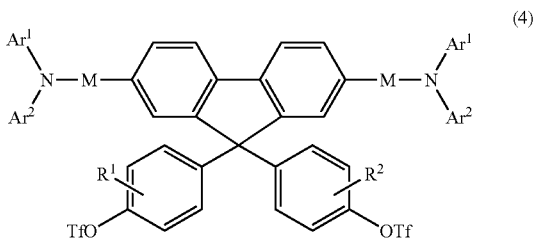

(4)

wherein $R^1$ and $R^2$ each independently represents hydrogen atom, a linear, branched or cyclic alkyl group or alkoxy group, an aryl group, an aryloxy group or a halogen atom; $Ar^1$ and $Ar^2$ each independently represents a substituted or unsubstituted aryl group or heteroaryl group, and may form a nitrogen-containing heterocyclic ring together with the nitrogen atom bonded thereto; M represents a single bond, an arylene group or a heteroarylene group; and Tf represents trifluoromethanesulfonyl group.

$Ar^3$—B(OH)$_2$ (5)

wherein $Ar^3$ represents a substituted or unsubstituted phenyl group, naphthyl group, biphenylyl group, terphenylyl group, anthryl group, fluorenyl group or pyridyl group (except for amino-substituted groups).

The present invention further relates to an organic electroluminescence device comprising using the amine compound in either of a luminescent layer, a hole transport layer or a hole injection layer.

BEST MODE FOR CARRYING OUT THE INVENTION

Figure 1:
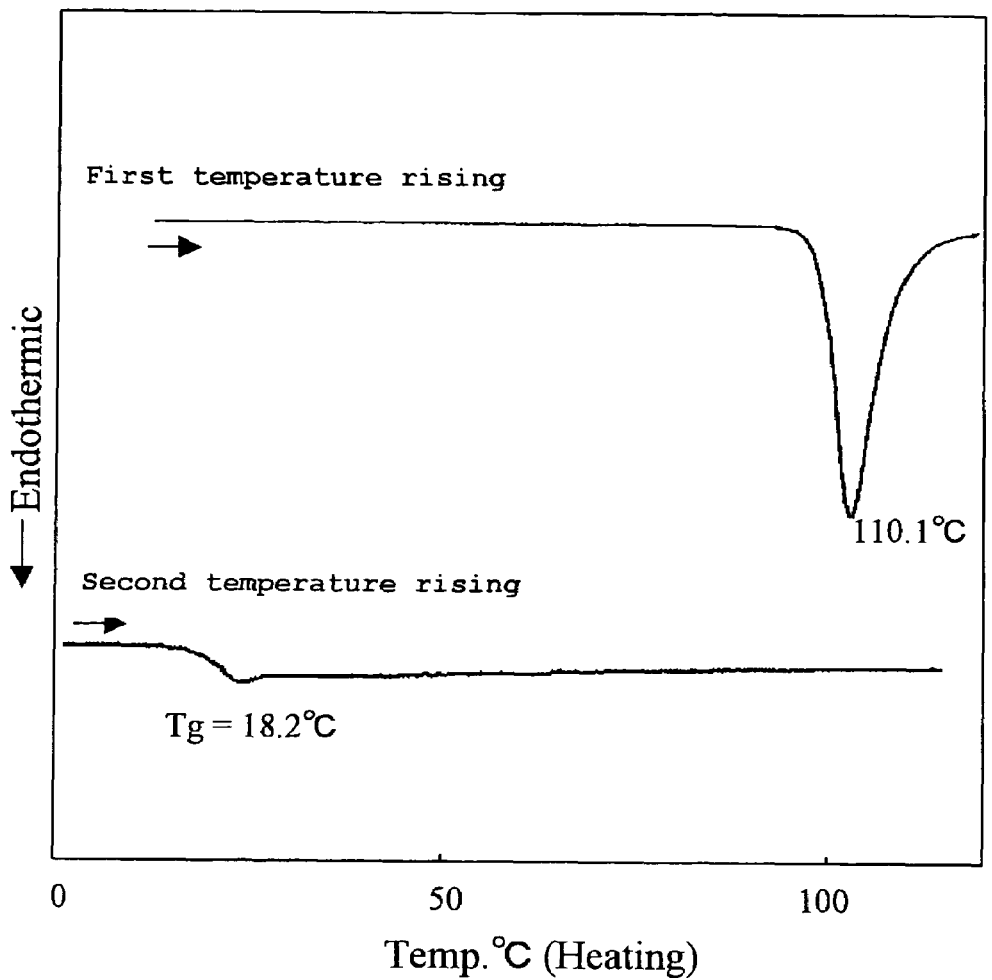
FIGS. 1, 2, 3 and 4 show charts of differential thermal analysis of the respective compounds obtained in Example 1 and Comparative Examples 1-3.

The present invention will be described in detail below.

In the amine compound represented by the general formula (1), $Ar^1$ and $Ar^2$ each independently represents a substituted or unsubstituted aryl group or heteroaryl group, and may form a nitrogen-containing heterocyclic ring together with the nitrogen atom bonded thereto.

The substituted or unsubstituted aryl groups are aromatic groups having from 6 to 24 carbon atoms, which may have substituents. Specific examples include phenyl group, 1-naphthyl group, 2-naphthyl group, 2-anthryl group, 9-anthryl group, 2-fluorenyl group, phenanthryl group, pyrenyl group, chrysenyl group, perillenyl group, picenyl group, 4-methylphenyl group, 3-methylphenyl group, 2-methylphenyl group, 4-ethylphenyl group, 3-ethylphenyl group, 2-ethylphenyl group, 4-n-propylphenyl group, 4-isopropylphenyl group, 2-isopropylphenyl group, 4-n-butylphenyl group, 4-isobutylphenyl group, 4-sec-butylphenyl group, 2-sec-butylphenyl group, 4-tert-butylphenyl group, 3-tert-butylphenyl group, 2-tert-butylphenyl group, 4-n-pentylphenyl group, 4-isopentylphenyl group, 2-neopentylphenyl group, 4-tert-pentylphenyl group, 4-n-hexylphenyl group, 4-(2'-ethylbutyl)phenyl group, 4-n-heptylphenyl group, 4-n-octylphenyl group, 4-(2'-ethylhexyl)phenyl group, 4-tert-octylphenyl group, 4-n-decylphenyl group, 4-n-dodecylphenyl group, 4-n-tetradecylphenyl group, 4-cyclopentylphenyl group, 4-cyclohexylphenyl group, 4-(4'-methylcyclohexyl)phenyl group, 4-(4'-tert-butylcyclohexyl)phenyl group, 3-cyclohexylphenyl group, 2-cyclohexylphenyl group, 4-ethyl-1-naphthyl group, 6-n-butyl-2-naphthyl group, 2,4-dimethylphenyl group, 2,5-dimethylphenyl group, 3,4-dimethylphenyl group, 3,5-dimethylphenyl group, 2,6-dimethylphenyl group, 2,4-diethylphenyl group, 2,3,5-trimethylphenyl group, 2,3,6-trimethylphenyl group, 3,4,5-trimethylphenyl group, 2,6-diethylphenyl group, 2,5-diisopropylphenyl group, 2,6-diisobutylphenyl group, 2,4-di-tert-butylphenyl group, 2,5-di-tert-butylphenyl group, 4,6-di-tert-butyl-2-methylphenyl group, 5-tert-butyl-2-methylphenyl group, 4-tert-butyl-2,6-dimethylphenyl group, 9-methyl-2-fluorenyl group, 9-ethyl-2-fluorenyl group, 9-n-hexyl-2-fluorenyl group, 9,9-dimethyl-2-fluorenyl group, 9,9-diethyl-2-fluorenyl group, 9,9-di-n-propyl-2-fluorenyl group, 4-methoxyphenyl group, 3-methoxyphenyl group, 2-methoxyphenyl group, 4-ethoxyphenyl group, 3-ethoxyphenyl group, 2-ethoxyphenyl group, 4-n-propoxyphenyl group, 3-n-propoxyphenyl group, 4-isopropoxyphenyl group, 2-isopropoxyphenyl group, 4-n-butoxyphenyl group, 4-isobutoxyphenyl group, 2-sec-butoxyphenyl group, 4-n-pentyloxyphenyl group, 4-isopentyloxyphenyl group, 2-isopentyloxyphenyl group, 4-neopentyloxyphenyl group, 2-neopentyloxyphenyl group, 4-n-hexyloxyphenyl group, 2-(2'-ethylbutyl)oxyphenyl group, 4-n-octyloxyphenyl group, 4-n-decyloxyphenyl group, 4-n-dodecyloxyphenyl group, 4-n-tetradecyloxyphenyl group, 4-cyclohexyloxyphenyl group, 2-cyclohexyloxyphenyl group, 2-methoxy-1-naphthyl group, 4-methoxy-1-naphthyl group, 4-n-butoxy-1-naphthyl group, 5-ethoxy-1-naphthyl group, 6-methoxy-2-naphthyl group, 6-ethoxy-2-naphthyl group, 6-n-butoxy-2-naphthyl group, 6-n-hexyloxy-2-naphthyl group, 7-methoxy-2-naphthyl group, 7-n-butoxy-2-naphthyl group, 2-methyl-4-methoxyphenyl group, 2-methyl-5-methoxyphenyl group, 3-methyl-4-methoxyphenyl group, 3-methyl-5-methoxyphenyl group, 3-ethyl-5-methoxyphenyl group, 2-methoxy-4-methylphenyl group, 3-methoxy-4-methylphenyl group, 2,4-dimethoxyphenyl group, 2,5-dimethoxyphenyl group, 2,6- dimethoxyphenyl group, 3,4-dimethoxyphenyl group, 3,5-dimethoxyphenyl group, 3,5-diethoxyphenyl group, 3,5-di-n-butoxyphenyl group, 2-methoxy-4-ethoxyphenyl group, 2-methoxy-6-ethoxyphenyl group, 3,4,5-trimethoxyphenyl group, 4-biphenylyl group, 3-biphenylyl group, 2-biphenylyl group, 4-(4'-methylphenyl)phenyl group, 4-(3'-methylphenyl)phenyl group, 4-(4'-methoxyphenyl)phenyl group, 4-(4'-n-butoxyphenyl)phenyl group, 2-(2'-methoxyphenyl)phenyl group, 4-(4'-chlorophenyl)phenyl group, 3-methyl-4-phenylphenyl group, 3-methoxy-4-phenylphenyl group, terphenyl group, 3,5-diphenylphenyl group, 10-phenylanthryl group, 10-(3,5-diphenylphenyl)-9-anthryl group, 9-phenyl-2-fluorenyl group, 4-fluorophenyl group, 3-fluorophenyl group, 2-fluorophenyl group, 4-chlorophenyl group, 3-chlorophenyl group, 2-chlorophenyl group, 4-bromophenyl group, 2-bromophenyl group, 4-chloro-1-naphthyl group, 4-chloro-2-naphthyl group, 6-bromo-2-naphthyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3-dichlorophenyl group, 2,4-dichlorophenyl group, 2,5-dichlorophenyl group, 3,4-dichlorophenyl group, 3,5-dichlorophenyl group, 2,5-dibromophenyl group, 2,4,6-trichlorophenyl group, 2,4-dichloro-1-naphthyl group, 1,6-dichloro-2-naphthyl group, 2-fluoro-4-methylphenyl group, 2-fluoro-5-methylphenyl group, 3-fluoro-2-methylphenyl group, 3-fluoro-4-methylphenyl group, 2-methyl-4-fluorophenyl group, 2-methyl-5-fluorophenyl group, 3-methyl-4-fluorophenyl group, 2-chloro-4-methylphenyl group, 2-chloro-5-methylphenyl group, 2-chloro-6-methylphenyl group, 2-methyl-3-chlorophenyl group, 2-methyl-4-chlorophenyl group, 3-chloro-4-methylphenyl group, 3-methyl-4-chlorophenyl group, 2-chloro-4,6-dimethylphenyl group, 2-methoxy-4-fluorophenyl group, 2-fluoro-4-methoxyphenyl group, 2-fluoro-4-ethoxyphenyl group, 2-fluoro-6-methoxyphenyl group, 3-fluoro-4-ethoxyphenyl group, 3-chloro-4-methoxyphenyl group, 2-methoxy-5-chlorophenyl group, 3-methoxy-6-chlorophenyl group, and 5-chloro-2,4-dimethoxyphenyl group. However, the substituted or unsubstituted aryl groups are not limited to those.

The substituted or unsubstituted heteroaryl groups are aromatic groups containing at least one hetero atom of oxygen atom, nitrogen atom, and sulfur atom. Examples thereof include 4-quinolyl group, 4-pyridyl group, 3-pyridyl group, 2-pyridyl group, 3-furyl group, 2-furyl group, 3-thienyl group, 2-thienyl group, 2-oxazolyl group, 2-thiazolyl group, 2-benzoxazolyl group, 2-benzothiazolyl group, and 2-benzoimidazolyl group. However, the substituted or unsubstituted heteroaryl groups are not limited to those.

To attain high Tg, it is preferable that at least one of $Ar^1$ and $Ar^2$ is a substituted or unsubstituted condensed ring aromatic group. Examples thereof include naphthyl group, phenanthryl group, fluorenyl group, anthryl group, pyrenyl group, chrysenyl group, picenyl group, and perillenyl group. Further preferred examples include 1-naphthyl group, 9-phenanthryl group, pyrenyl group, and 2-fluorenyl group. In the case of the amine compound represented by the general formula (1) wherein at least one of $Ar^1$ and $Ar^2$ is a substituted or unsubstituted condensed ring aromatic group having carbon atoms exceeding 16, the yield at the time of synthesis tends to decrease or isomers tend to remain in an amount of several thousands ppm. Therefore, there is the case that $Ar^1$ and $Ar^2$ are preferably either of phenyl group, 4-methylphenyl group, 4-biphenylyl group or 1-naphthyl group.

In the amine compound represented by the general formula (1), $Ar^1$ and $Ar^2$ may form a nitrogen-containing heterocyclic ring together with the nitrogen atom bonded thereto, and may form a substituted or unsubstituted —N-carbazolyl group, —N-phenoxazinyl group or —N-phenothiazinyl group. The nitrogen-containing heterocyclic ring may be monosubstituted or polysubstituted with a substituent such as a halogen atom, an alkyl group having from 1 to 10 carbon atoms, an alkoxy group having from 1 to 10 carbon atoms, and an aryl group having from 6 to 10 carbon atoms. Above all, an unsubstituted —N-carbazolyl group, —N-phenoxazinyl group or —N-phenothiazinyl group; or —N-carbazolyl groups, —N-phenoxazinyl groups or —N-phenothiazinyl groups monosubstituted or polysubstituted with a halogen atom, an alkyl group having from 1 to 4 carbon atoms, an alkoxy group having from 1 to 4 carbon atoms, or an aryl group having from 6 to 10 carbon atoms are preferable, with unsubstituted —N-carbazolyl groups, —N-phenoxazinyl groups or —N-phenothiazinyl groups being more preferable. Specific examples of substituted —N-carbazolyl groups, —N-phenoxazinyl groups or —N-phenothiazinyl groups include 2-methyl-N-carbazolyl group, 3-methyl-N-carbazolyl group, 4-methyl-N-carbazolyl group, 3-n-butyl-N-carbazolyl group, 3-n-hexyl-N-carbazolyl group, 3-n-octyl-N-carbazolyl group, 3-n-decyl-N-carbazolyl group, 3,6-dimethyl-N-carbazolyl group, 2-methoxy-N-carbazolyl group, 3-methoxy-N-carbazolyl group, 3-ethoxy-N-carbazolyl group, 3-isopropoxy-N-carbazolyl group, 3-n-butoxy-N-carbazolyl group, 3-n-octyloxy-N-carbazolyl group, 3-n-decyloxy-N-carbazolyl group, 3-phenyl-N-carbazolyl group, 3-(4'-methylphenyl)-N-carbazolyl group, 3-(4'-tert-butylphenyl)-N-carbazolyl group, 3-chloro-N-carbazolyl group, and 2-methyl-N-phenothiazinyl group.

$Ar^3$ each independently represents a substituted or unsubstituted phenyl group, naphthyl group, biphenylyl group, terphenylyl group, anthryl group, fluorenyl group or pyridyl group (except for amino-substituted groups). Examples of the substitutent for $Ar^3$ include an alkyl group such as methyl group, ethyl group or propyl group; an alkoxyl group such as methoxy group, ethoxy group or propoxy group; an aryl group such as phenyl group; an aryloxy group such as phenoxy group; and a heteroaryl group such as pyridyl group. Of those, preferable substituents for $Ar^3$ include phenyl group, 3,5-diphenylphenyl group, 1-naphthyl group, 4-biphenylyl group, 4-terphenylyl group, 9-anthryl group, 10-phenyl-9-anthryl group or 10-(3,5-diphenylphenyl)-9-anthryl group.

In the amine compound represented by the general formula (1), $R^1$ and $R^2$ each independently represents hydrogen atom, a linear, branched or cyclic alkyl group or alkoxy group, an aryl group, an aryloxy group or a halogen atom.

Examples of the alkyl group include linear, branched or cyclic alkyl groups having from 1 to 18 carbon atoms. Specific examples include methyl group, ethyl group, propyl group, isopropyl group, butyl group, sec-butyl group, tert-butyl group, pentyl group, hexyl group, heptyl group, octyl group, stearyl group, trichloromethyl group, trifluoromethyl group, cyclopropyl group, cyclohexyl group, 1,3-cyclohexadienyl group, and 2-cyclopenten-1-yl group.

Examples of the alkoxy group include linear, branched or cyclic alkoxy groups having from 1 to 18 carbon atoms. Specific examples include methoxy group, ethoxy group, propoxy group, isopropoxy group, n-butoxy group, sec-butoxy group, tert-butoxy group, pentyloxy group, hexyloxy group, stearyloxy group, and trifluoromethoxy group.

Examples of the aryl group include aromatic groups having from 6 to 24 carbon atoms, which may have substituents. Specific examples include the same substituents as described previously for $Ar^1$ or $Ar^2$, such as phenyl group, 4-methylphenyl group, 3-methylphenyl group, 2-methylphenyl group, 4-ethylphenyl group, 3-ethylphenyl group, 2-ethylphenyl group, 4-n-propylphenyl group, 4-n-butylphenyl group, 4-isobutylphenyl group, 4-tert-butylphenyl group, 4-cyclopentylphenyl group, 4-cyclohexylphenyl group, 2,4-dimethylphenyl group, 3,5-dimethylphenyl group, 3,4-dimethylphenyl group, 1-biphenyl group, 1-naphthyl group, 2-naphthyl group, 9-phenanthryl group, 9,9-dialkyl-fluoren-2-yl group, and 9,9-di-trifluoromethyl-fluoren-2-yl group.

Examples of the aryloxy group include aromatic groups having from 6 to 24 carbon atoms, which may have substituents. Specific examples include phenoxy group, p-tert-butylphenoxy group, 3-fluorophenoxy group, and 4-fluorophenoxy group.

Examples of the halogen atom include fluorine atom, chlorine atom, bromine atom, and iodine atom.

In the amine compound represented by the general formula (1), M represents a single bond, an arylene group or a heteroarylene group. Examples of the arylene group include phenylene group, 1,4-naphthalenediyl group, 4,4'-biphenyldiyl group, 4,4'-terphenyldiyl group, 2,6group, 9,10-anthracenediyl group, and 2,7-naphthalenediyl -9,9'-dialkylfluorenediyl group. Examples of the heteroarylene group include 2,5-thiophenediyl group, 5,5'-2,2'-bithiophenediyl group, 4,7-benzothiadiazolediyl group, 2,5-oxadiazolediyl group, 3,5-4-phenyl-triazole group, 2,6-pyridinediyl group and 6,6'-2,2'-bipyridinediyl group.

Further examples can include the substituents in which the aryl groups link, represented by the following general formulae (2a) to (2f).

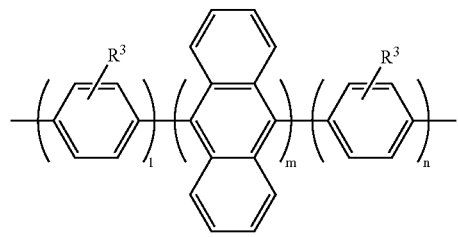
(2a)

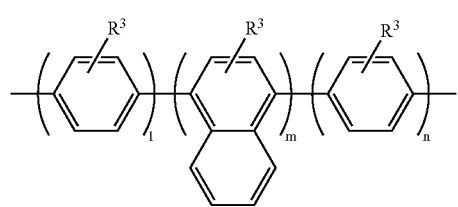
(2b)

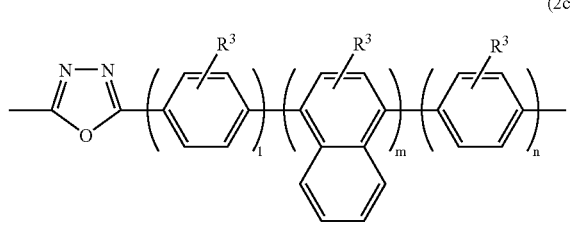
(2c)

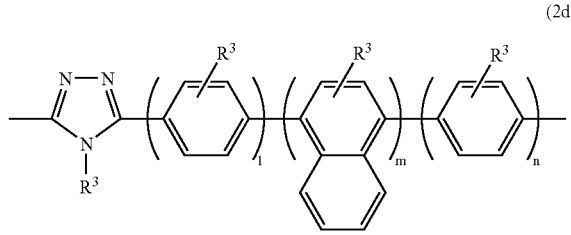
(2d)

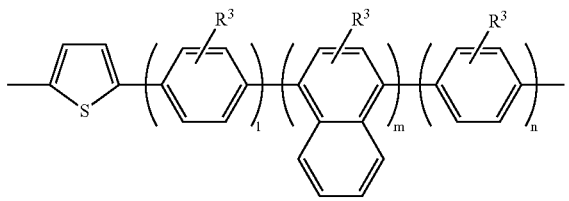
(2e)

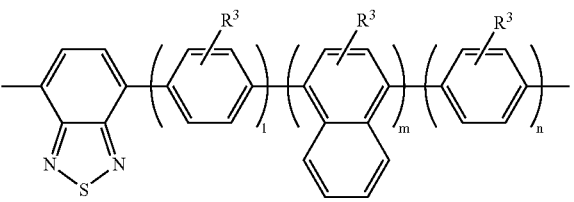
(2f)

wherein $R^3$ represents hydrogen atom, an alkyl group or alkoxy group having from 1 to 18 carbon atoms, or an aryl group having from 6 to 12 carbon atoms; and l, m and n represent a positive integer satisfying $1 \leq l+m+n \leq 4$.

Specific examples of $R^3$ include an alkyl group such as methyl group, ethyl group, propyl group, isopropyl group, butyl group, sec-butyl group, tert-butyl group, pentyl group, hexyl group, heptyl group or octyl group; an alkoxy group such as methoxy group, ethoxy group, propoxy group, isopropoxy group, n-butoxy group, sec-butoxy group, tert-butoxy group, pentyloxy group or hexyloxy group; and an aryl group such as phenyl group, 4-methylphenyl group, 3-methylphenyl group, 2-methylphenyl group, 4-ethylphenyl group, 3-ethylphenyl group, 2-ethylphenyl group, 4-n-propylphenyl group, 4-n-butylphenyl group, 4-isobutylphenyl group, 4-tert-butylphenyl group, 4-cyclopentylphenyl group, 4-cyclohexylphenyl group, 1-biphenyl group, 1-naphthyl group and 2-naphthyl group.

Of the compounds represented by the general formula (1), an amine compound wherein $R^1$ and $R^2$ are hydrogen atom, particularly an amine compound wherein M represents a single bond, represented by the following general formula (3), is preferable.

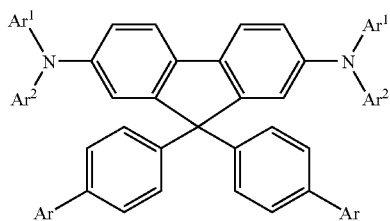
(3)

wherein $Ar^1$ and $Ar^2$ each independently represents a substituted or unsubstituted aryl group or heteroaryl group, and may form a nitrogen-containing heterocyclic ring together with the nitrogen atom bonded thereto; and Ar represents phenyl group, 4-methylphenyl group, 3,5-diphenylphenyl group, 1-naphthyl group, 4-biphenylyl group, 4-terphenylyl group, 9-anthryl group, 10-phenyl-9-anthryl group or 10-(3,5-diphenylphenyl)-9-anthryl group.

Above all, amine compounds wherein Ar¹ and Ar² are phenyl group, 4-methylphenyl group, 4-biphenylyl group or 1-naphthyl group are preferable.

Specific examples of the amine compound represented by the general formula (1) are shown in Tables 1 to 11 below, but the present invention is not limited to those compounds.

TABLE 1

| Compound | Ar¹ | Ar² | Ar³ | R¹ | R² | M |
|---|---|---|---|---|---|---|
| 1 | 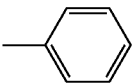 | 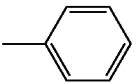 | 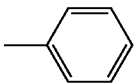 | H | H | Single bond |
| 2 | 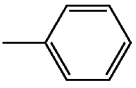 | 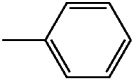 | 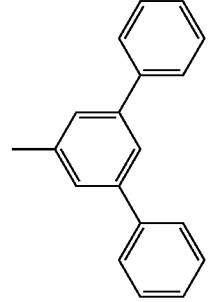 | H | H | Single bond |
| 3 | 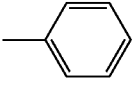 | 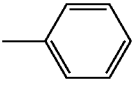 | 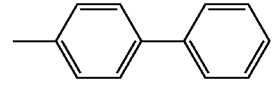 | H | H | Single bond |
| 4 | 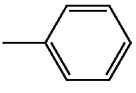 | 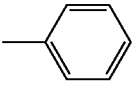 | 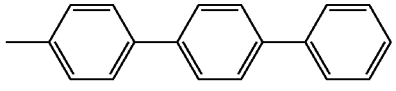 | H | H | Single bond |
| 5 | 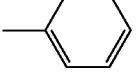 | 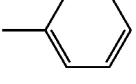 | 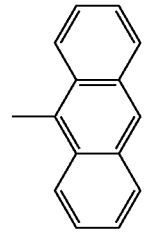 | H | H | Single bond |
| 6 | 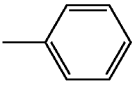 | 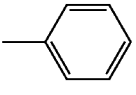 | 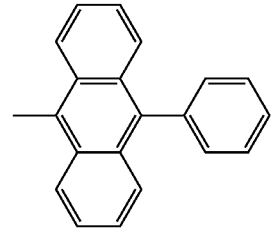 | H | H | Single bond |
| 7 | 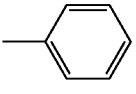 | 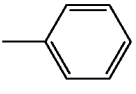 | 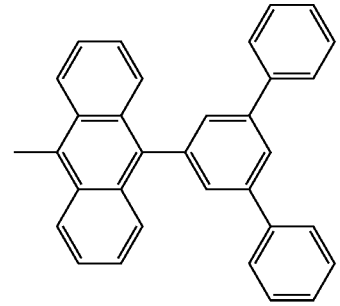 | H | H | Single bond |

TABLE 1-continued

| Compound | Ar¹ | Ar² | Ar³ | R¹ | R² | M |
|---|---|---|---|---|---|---|
| 8 | phenyl | phenyl | 9,9-dimethylfluorenyl | H | H | Single bond |
| 9 | 4-methylphenyl | 4-methylphenyl | phenyl | H | H | Single bond |
| 10 | phenyl | naphthyl | phenyl | H | H | Single bond |
| 11 | phenyl | biphenyl | phenyl | H | H | Single bond |
| 12 | biphenyl | biphenyl | phenyl | H | H | Single bond |
| 13 | phenyl | naphthyl | phenyl | H | H | Single bond |

TABLE 2

| Compound | Ar¹ | Ar² | Ar³ | R¹ | R² | M |
|---|---|---|---|---|---|---|
| 14 | 4-methylphenyl | 4-methylphenyl | 3,5-diphenylphenyl | H | H | Single bond |
| 15 | 4-methylphenyl | 4-methylphenyl | biphenyl | H | H | Single bond |
| 16 | 4-methylphenyl | 4-methylphenyl | terphenyl | H | H | Single bond |

TABLE 2-continued

| Compound | Ar¹ | Ar² | Ar³ | R¹ | R² | M |
| --- | --- | --- | --- | --- | --- | --- |
| 17 | -C₆H₄-CH₃ (p-tolyl) | -C₆H₄-CH₃ (p-tolyl) | 9-anthracenyl | H | H | Single bond |
| 18 | -C₆H₄-CH₃ (p-tolyl) | -C₆H₄-CH₃ (p-tolyl) | 10-phenyl-9-anthracenyl | H | H | Single bond |
| 19 | -C₆H₄-CH₃ (p-tolyl) | -C₆H₄-CH₃ (p-tolyl) | 10-(3,5-diphenylphenyl)-9-anthracenyl | H | H | Single bond |
| 20 | -C₆H₄-CH₃ (p-tolyl) | -C₆H₄-CH₃ (p-tolyl) | 9,9-dimethylfluorenyl | H | H | Single bond |
| 21 | -C₆H₄-CH₃ (o-tolyl) | -C₆H₄-CH₃ (o-tolyl) | phenyl | H | H | Single bond |
| 22 | 4-(diphenylamino)phenyl | phenyl | phenyl | H | H | Single bond |

TABLE 3

| Compound | Ar¹ | Ar² | Ar³ | R¹ | R² | M |
|---|---|---|---|---|---|---|
| 23 | phenyl | phenyl | phenyl | H | H | p-phenylene |
| 24 | phenyl | phenyl | biphenyl-4-yl | H | H | p-phenylene |
| 25 | phenyl | phenyl | p-terphenyl-4-yl | H | H | p-phenylene |
| 26 | phenyl | phenyl | anthracen-9-yl | H | H | p-phenylene |
| 27 | phenyl | phenyl | 10-phenylanthracen-9-yl | H | H | p-phenylene |
| 28 | phenyl | phenyl | 9,9-dimethylfluoren-2-yl | H | H | p-phenylene |
| 29 | 4-methylphenyl | 4-methylphenyl | phenyl | H | H | p-phenylene |
| 30 | phenyl | naphthalen-1-yl | phenyl | H | H | p-phenylene |
| 31 | phenyl | biphenyl-4-yl | phenyl | H | H | p-phenylene |
| 32 | biphenyl-4-yl | biphenyl-4-yl | phenyl | H | H | p-phenylene |

TABLE 3-continued

| Compound | Ar¹ | Ar² | Ar³ | R¹ | R² | M |
|---|---|---|---|---|---|---|
| 33 | phenyl | 2-naphthyl | phenyl | H | H | 1,4-phenylene |

TABLE 4

| Compound | Ar¹ | Ar² | Ar³ | R¹ | R² | M |
|---|---|---|---|---|---|---|
| 34 | phenyl | phenyl | phenyl | H | H | 4,4'-biphenylene |
| 35 | phenyl | phenyl | 4-biphenyl | H | H | 4,4'-biphenylene |
| 36 | phenyl | phenyl | 4-(4-biphenyl)phenyl | H | H | 4,4'-biphenylene |
| 37 | phenyl | phenyl | 9-anthryl | H | H | 4,4'-biphenylene |
| 38 | phenyl | phenyl | 10-phenyl-9-anthryl | H | H | 4,4'-biphenylene |
| 39 | phenyl | phenyl | 9,9-dimethyl-2-fluorenyl | H | H | 4,4'-biphenylene |
| 40 | 4-methylphenyl | 4-methylphenyl | phenyl | H | H | 4,4'-biphenylene |
| 41 | phenyl | 1-naphthyl | phenyl | H | H | 4,4'-biphenylene |

TABLE 4-continued

| Compound | Ar¹ | Ar² | Ar³ | R¹ | R² | M |
|---|---|---|---|---|---|---|
| 42 | phenyl | biphenyl | phenyl | H | H | biphenyl |
| 43 | biphenyl | biphenyl | phenyl | H | H | biphenyl |
| 44 | phenyl | naphthyl | phenyl | H | H | biphenyl |

TABLE 5

| Compound | Ar¹ | Ar² | Ar³ | R¹ | R² | M |
|---|---|---|---|---|---|---|
| 45 | phenyl | phenyl | phenyl | H | H | 9,9-dimethylfluorenyl |
| 46 | phenyl | phenyl | biphenyl | H | H | 9,9-dimethylfluorenyl |
| 47 | phenyl | phenyl | terphenyl | H | H | 9,9-dimethylfluorenyl |
| 48 | phenyl | phenyl | anthracenyl | H | H | 9,9-dimethylfluorenyl |
| 49 | phenyl | phenyl | 10-phenylanthracenyl | H | H | 9,9-dimethylfluorenyl |
| 50 | phenyl | phenyl | 9,9-dimethylfluorenyl | H | H | 9,9-dimethylfluorenyl |

TABLE 5-continued
| Compound | Ar¹ | Ar² | Ar³ | R¹ | R² | M |
|---|---|---|---|---|---|---|
| 51 | 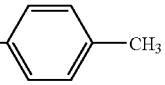 | 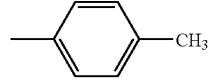 | 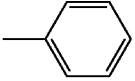 | H | H | 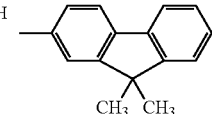 |
| 52 | 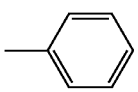 | 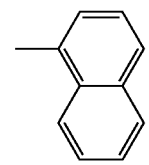 | 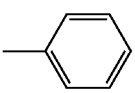 | H | H | 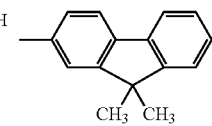 |
| 53 | 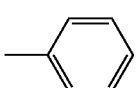 | 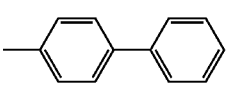 | 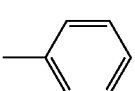 | H | H | 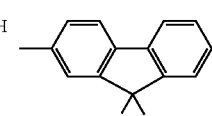 |
| 54 | 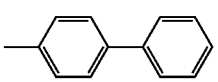 | 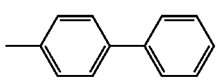 | 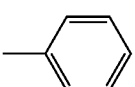 | H | H | 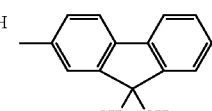 |
| 55 | 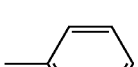 | 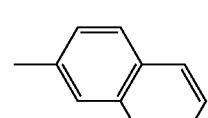 | 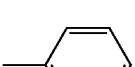 | H | H | 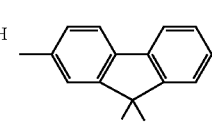 |
TABLE 6
| Compound | Ar¹ | Ar² | Ar³ | R¹ | R² | M |
|---|---|---|---|---|---|---|
| 56 | 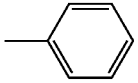 | 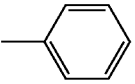 | 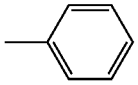 | H | H | 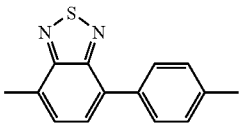 |
| 57 | 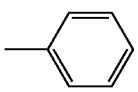 | 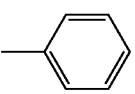 | 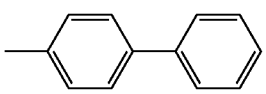 | H | H | 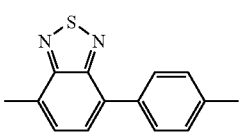 |
| 58 | 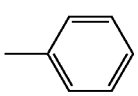 | 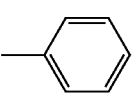 | 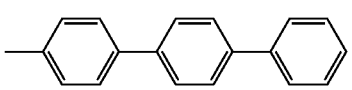 | H | H | 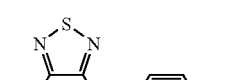 |
| 59 | 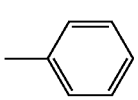 | 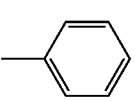 |  | H | H | 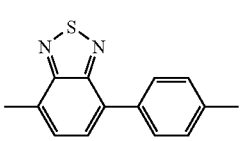 |

TABLE 6-continued
| Compound | Ar¹ | Ar² | Ar³ | R¹ | R² | M |
|---|---|---|---|---|---|---|
| 60 | 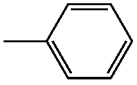 | 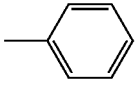 | 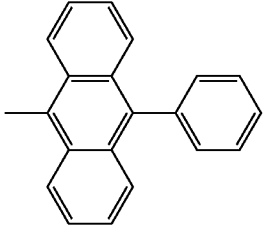 | H | H | 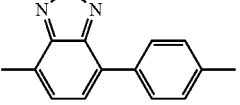 |
| 61 | 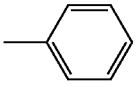 | 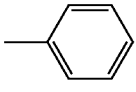 | 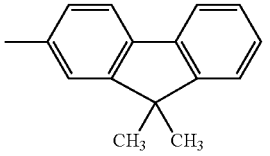 | H | H | 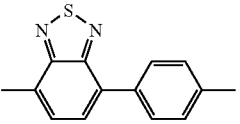 |
| 62 | 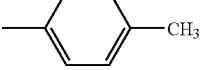 | 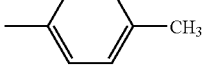 | 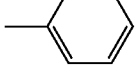 | H | H | 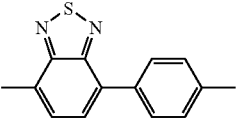 |
| 63 | 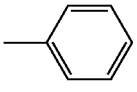 | 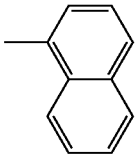 | 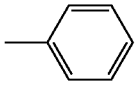 | H | H | 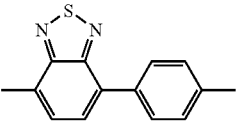 |
| 64 | 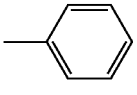 | 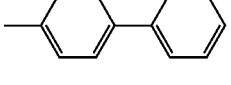 | 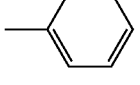 | H | H | 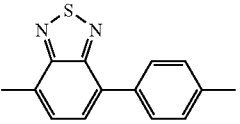 |
| 65 | 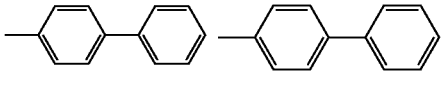 | 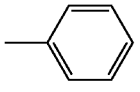 | 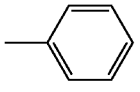 | H | H | 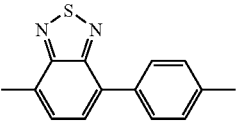 |
| 66 | 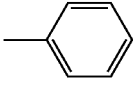 | 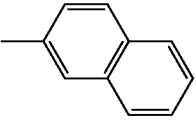 | 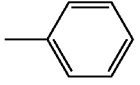 | H | H | 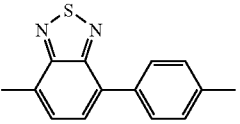 |
TABLE 7
| Compound | Ar¹ | Ar² | Ar³ |
|---|---|---|---|
| 67 | 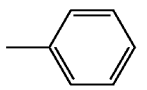 | 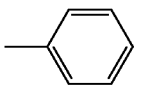 | 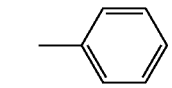 |
| 68 | 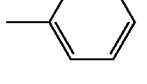 | 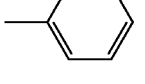 | 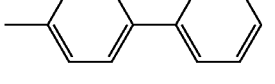 |

TABLE 7-continued

TABLE 7-continued

| Compound | R¹ | R² | M |
|---|---|---|---|
| 67 | H | H | |
| 68 | H | H | |
| 69 | H | H | |
| 70 | H | H | |
| 71 | H | H | |
| 72 | H | H | |

TABLE 7-continued
| | | | |
|---|---|---|---|
| 73 | H | H | 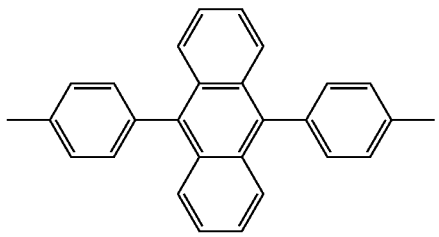 |
| 74 | H | H | 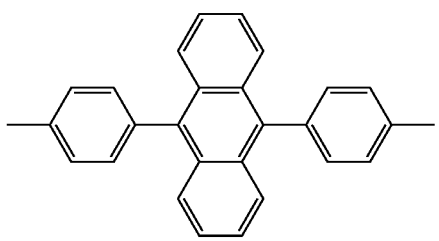 |
| 75 | H | H | 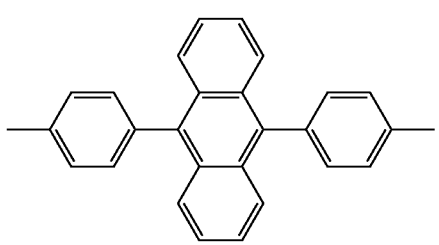 |
| 76 | H | H | 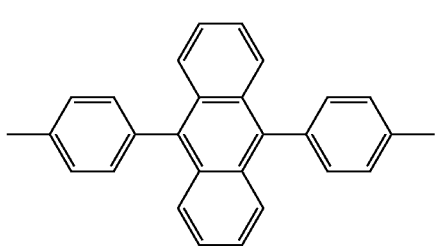 |
| 77 | H | H | 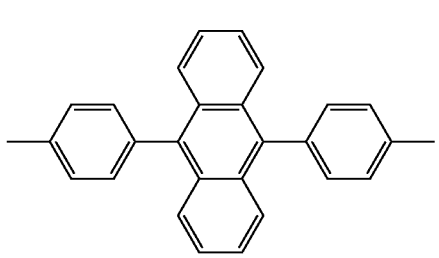 |
TABLE 8
| Compound | $Ar^1$ | $Ar^2$ | $Ar^3$ | $R^1$ | $R^2$ | M |
|---|---|---|---|---|---|---|
| 78 | 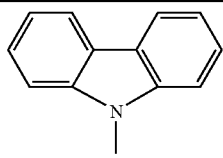 | | 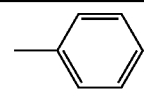 | H | H | Single bond |

TABLE 8-continued

| Compound | Ar¹ | Ar² | Ar³ | R¹ | R² | M |
|---|---|---|---|---|---|---|
| 79 | carbazol-9-yl | | phenylene | H | H | p-phenylene |
| 80 | carbazol-9-yl | | biphenyl-4,4'-diyl | H | H | Single bond |
| 81 | carbazol-9-yl | | p-terphenyl-4,4''-diyl | H | H | Single bond |
| 82 | carbazol-9-yl | | anthracen-9-yl | H | H | Single bond |
| 83 | carbazol-9-yl | | 10-phenylanthracen-9-yl | H | H | Single bond |
| 84 | carbazol-9-yl | | 9,9-dimethylfluorene-2,7-diyl | H | H | Single bond |

TABLE 9

| Compound | Ar¹ | Ar² | Ar³ | R¹ | R² | M |
|---|---|---|---|---|---|---|
| 85 | phenyl | phenylene | phenylene | H | H | thiophene-phenylene |
| 86 | phenyl | phenylene | biphenyl-4,4'-diyl | H | H | thiophene-phenylene |

TABLE 9-continued

| Compound | Ar¹ | Ar² | Ar³ | R¹ | R² | M |
|---|---|---|---|---|---|---|
| 87 | phenyl | phenyl | p-terphenyl | H | H | thiophene-phenyl |
| 88 | phenyl | phenyl | anthracen-9-yl | H | H | thiophene-phenyl |
| 89 | phenyl | phenyl | 10-phenylanthracen-9-yl | H | H | thiophene-phenyl |
| 90 | phenyl | phenyl | 9,9-dimethylfluoren-2-yl | H | H | thiophene-phenyl |
| 91 | 4-methylphenyl | 4-methylphenyl | phenyl | H | H | thiophene-phenyl |
| 92 | phenyl | naphthalen-1-yl | phenyl | H | H | thiophene-phenyl |
| 93 | phenyl | biphenyl-4-yl | phenyl | H | H | thiophene-phenyl |
| 94 | biphenyl-4-yl | biphenyl-4-yl | phenyl | H | H | thiophene-phenyl |
| 95 | phenyl | naphthalen-2-yl | phenyl | H | H | thiophene-phenyl |

TABLE 10

| Compound | Ar¹ | Ar² | Ar³ |
|---|---|---|---|
| 96 | phenyl | phenyl | phenyl |
| 97 | phenyl | phenyl | biphenyl |
| 98 | phenyl | phenyl | p-terphenyl |
| 99 | phenyl | phenyl | 9-anthryl |
| 100 | phenyl | phenyl | 10-phenyl-9-anthryl |
| 101 | phenyl | phenyl | 9,9-dimethylfluoren-2-yl |
| 102 | 4-methylphenyl | 4-methylphenyl | phenyl |
| 103 | phenyl | 1-naphthyl | phenyl |
| 104 | phenyl | biphenyl | phenyl |
| 105 | biphenyl | biphenyl | phenyl |

TABLE 10-continued
| | | | |
|---|---|---|---|
| 106 | 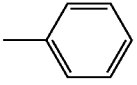 | 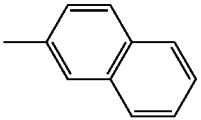 | 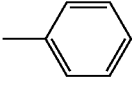 |
| Compound | R¹ | R² | M |
|---|---|---|---|
| 96 | H | H | 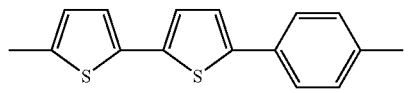 |
| 97 | H | H | 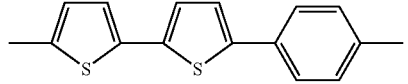 |
| 98 | H | H | 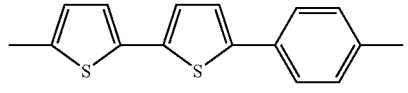 |
| 99 | H | H | 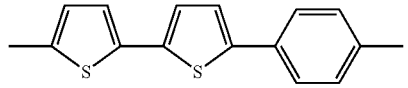 |
| 100 | H | H | 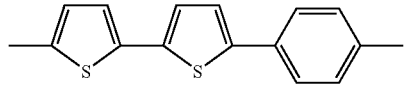 |
| 101 | H | H | 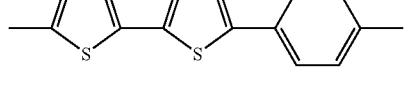 |
| 102 | H | H | 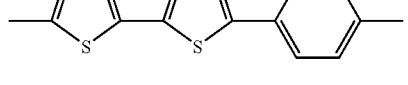 |
| 103 | H | H | 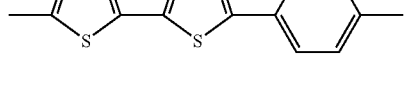 |
| 104 | H | H | 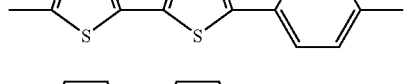 |
| 105 | H | H | 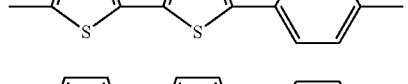 |
| 106 | H | H | 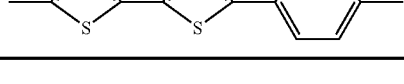 |
TABLE 11
| Compound | Ar¹ | Ar² | Ar³ |
|---|---|---|---|
| 107 | 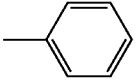 | 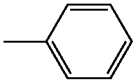 | 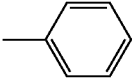 |

TABLE 11-continued

| Compound | R¹ | R² | M |
|---|---|---|---|
| 107 | H | H | (4,4'',4'''-terphenylene linker) |

(Structures 108–117 shown with R¹, R² substituents and M groups as depicted.)

TABLE 11-continued

| 108 | H | H | (structure) |
| 109 | H | H | (structure) |
| 110 | H | H | (structure) |
| 111 | H | H | (structure) |
| 112 | H | H | (structure) |
| 113 | H | H | (structure) |
| 114 | H | H | (structure) |
| 115 | H | H | (structure) |
| 116 | H | H | (structure) |
| 117 | H | H | (structure) |

The amine compound represented by the general formula (1) can be synthesized by reacting fluorene derivatives represented by the following general formula (4) and a boronic acid compound represented by the following general formula (5) in the presence of a palladium catalyst.

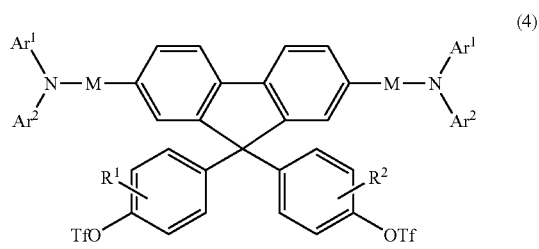

(4)

(5)

wherein $R^1$ and $R^2$ each independently represents hydrogen atom, a linear, branched or cyclic alkyl group or alkoxy group, an aryl group, an aryloxy group or a halogen atom; $Ar^1$ and $Ar^2$ each independently represents a substituted or unsubstituted aryl group or heteroaryl group, and may form a nitrogen-containing heterocyclic ring together with the nitrogen atom bonded thereto; M represents a single bond, an arylene group or a heteroarylene group; and Tf represents trifluoromethanesulfonyl group.

wherein $Ar^3$ represents a substituted or unsubstituted phenyl group, naphthyl group, biphenylyl group, terphenylyl group, anthryl group, fluorenyl group or pyridyl group (except for amino-substituted groups).

The fluorene derivatives represented by the general formula (4) can be synthesized by utilizing, for example, Suzuki coupling reaction (for example, see Chem. Rev. 1995, 95, p 2457-2483), or an amination reaction using a palladium catalyst (see Patent Document 15).

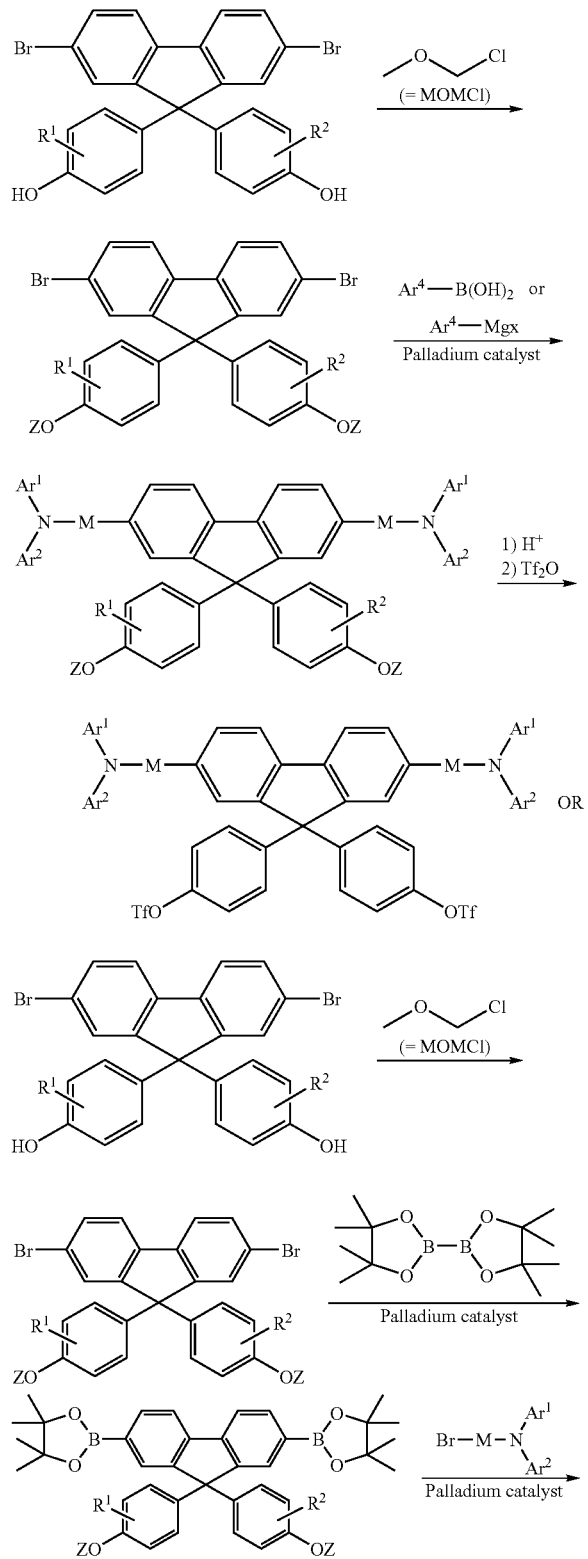

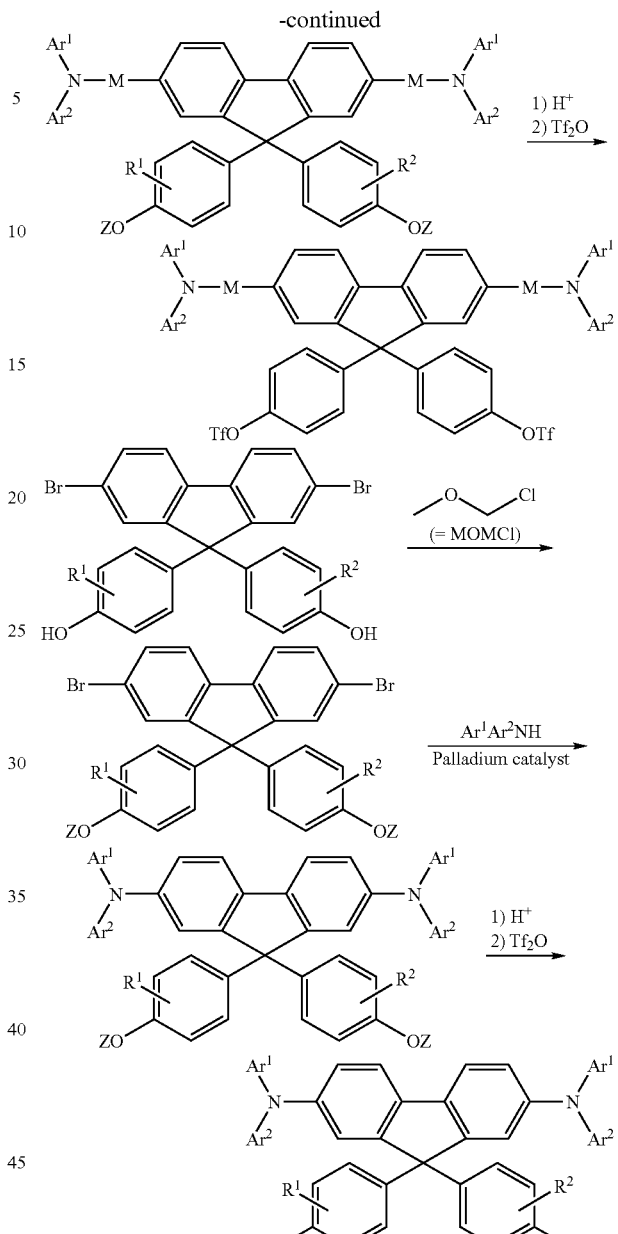

wherein $R^1$ and $R^2$ each independently represents hydrogen atom, a linear, branched or cyclic alkyl group or alkoxy group, an aryl group, an aryloxy group or a halogen atom; Z is not particularly limited so long as it is used as a protective group of a phenolic hydroxyl group, but is preferably methoxyethoxymethyl group or methoxymethyl group; and $Ar^4$ is a substituent represented by the following general formula (6), (6)

wherein $Ar^1$ and $Ar^2$ each independently represents a substituted or unsubstituted aryl group or heteroaryl group, and may form a nitrogen-containing heterocyclic ring together with the nitrogen atom bonded thereto; and M represents a single bond, an arylene group or a heteroarylene group.

The palladium catalyst used in the amine compound synthesis reaction is not particularly limited. Examples of the palladium catalyst include divalent palladium compounds such as palladium(II)chloride, palladium(II)bromide, palladium(II)acetate, palladium(II)acetylacetonate, dichlorobis(benzonitrile)palladium(II), dichlorobis(acetonitrile)palladium(II), dichlorobis(tri-phenylphosphine)palladium(II), dichlorotetraamminepalladium(II), dichloro(cycloocta-1,5-diene)palladium(II) or palladium(II)trifluoroacetate; and zerovalent palladium compounds such as tris(dibenzylideneacetone)dipalladium(0), tris(dibenzylideneacetone)dipalladium(0)-chloroform complex or tetrakis(triphenylphosphine)palladium(0). Further examples can include fixed palladium catalysts such as polymer-fixed palladium catalyst or palladium carbon. Reaction may be conducted in the co-presence of monodentate aryl phosphines such as triphenylphosphine or tri(o-tolyl)phosphine; monodentate alkylphosphines such as tri(cyclohexyl)phosphine, tri(isopropyl) phosphine or tri(tert-butyl)phosphine; and didentate phosphines such as 1,2-bis(diphenylphosphino)ethane, 1,2-bis(diphenyl-phosphino)propane, 1,2-bis(diphenylphosphino)butane or 1,2-bis(diphenylphosphino)ferrocene, in addition to the above catalysts.

The amount of the palladium catalyst used is not particularly limited, but is usually in the range of from 0.000001 to 20% by mole per mole of the fluorene derivatives represented by the general formula (4). When the amount of the catalyst falls within the above range, the amine compound can be synthesized in high selectivity. From the sense of reducing the amount of an expensive catalyst used, further preferable amount of the catalyst used is in a range of from 0.0001 to 5% by mole as converted to palladium per mole of the fluorene derivatives.

A base is used in the amine synthesis reaction according to the present invention. The base used may be selected from inorganic bases and/or organic bases, and is not particularly limited. Preferred examples include sodium hydroxide, potassium hydroxide, sodium carbonate, potassium carbonate, potassium phosphate, sodium phosphate, alkali metal alkoxides such as sodium methoxide, sodium ethoxide, potassium methoxide, potassium ethoxide, lithium tert-butoxide, sodium tert-butoxide or potassium tert-butoxide, triethylamine, tributylamine, and pyridine. Further preferable examples are sodium hydroxide, potassium hydroxide, sodium carbonate, potassium carbonate, potassium phosphate, and sodium phosphate.

The amount of the base used is preferably 0.5 times by mole or more to the fluorene derivatives represented by the general formula (4). Where the amount of the base is less than 0.5 times by mole, the yield of the amine compound may lower. Even where the base is added in large excess, the yield of the amine compound does not change, and the post-treatment operation after completion of the reaction becomes complicated. Accordingly, the amount of the base used is more preferably in a range of from 1 to 5 times by mole.

The reaction in the present invention is usually carried out in the presence of an inert solvent. As to the solvent used, any solvents may be used without particular limitations so far as they do not remarkably hinder the reaction. Examples of the solvents include aromatic organic solvents such as benzene, toluene or xylene; ether-based organic solvents such as diethyl ether, tetrahydrofuran (THF) or dioxane; acetonitrile; dimethylformamide (DMF); dimethyl sulfoxide; and hexamethyl phosphortriamide. Of those, aromatic organic solvents such as benzene, toluene or xylene are more preferable.

The reaction in the present invention can be carried out in an inert gas atmosphere such as nitrogen or argon under normal pressure, or can also be carried out under pressure.

The reaction in the present invention is carried out at a reaction temperature in a range of from 20 to 300° C., and preferably from 30 to 150° C.

The reaction time in the present invention is determined by the amounts of the fluorene derivatives, arylboronic acid, base and palladium catalyst, and the reaction temperature, but may be chosen from a range of from several minutes to 72 hours.

After completion of the reaction, the desired compound can be obtained by treating with the conventional methods.

The amine compounds having a fluorene group as a mother nucleus according to the present invention are different from conventional materials, and many of those have an amorphous structure when synthesizing the same. Hence, the compounds have an advantage such that the film stability is excellent. Accordingly, those compounds can be used not only as hole transport materials of organic EL devices, electrophotographic receptors, etc., but also in any fields of organic photoconductive materials such as photoelectric transfer devices, solar batteries or image sensors.

EXAMPLE

The present invention will be described in more detail by reference to the following Examples.

Glass transition temperature shown in the Examples was measured using SSC-5000, a product of Seiko Instruments Inc., under a temperature rising condition of 10° C./min.

$^1$H-NMR and $^{13}$C-NMR were measured using Gemini 200, a product of Varian, Inc.

FDMS was measured using M-80B, a product of Hitachi, Ltd.

Synthesis Example 1

0.82 g (34.2 mmol) of sodium hydride and 25 ml of THF were placed in a 100 ml eggplant type flask under nitrogen stream, and the resulting reaction solution was cooled to 0° C. THF solution of 6.5 g (14.3 mmol) of 2,7-dibromo-4,4'-(9-fluorenylidene)diphenol was added dropwise to the flask, and 5.3 g (42.7 mmol) of 2-methoxyethoxymethyl chloride was subsequently added dropwise thereto. The resulting mixture was stirred at room temperature for 12 hours, and 10 ml of methanol was added to decompose sodium hydride. Thereafter, 20 ml of toluene was added to separate an organic phase. Washing with water and a saturated sodium chloride solution was conducted, and then the organic phase was concentrated. By recrystallizing the concentrated liquid from ethanol, 2,7-dibromo-9,9'-bis[4-(2-methoxyethoxymethoxy)phenyl]-9H-fluorene (intermediate A) was isolated in an amount of 7.7 g (yield=80%). Identification was conducted with $^1$H-NMR and $^{13}$C-NMR.

Intermediate A

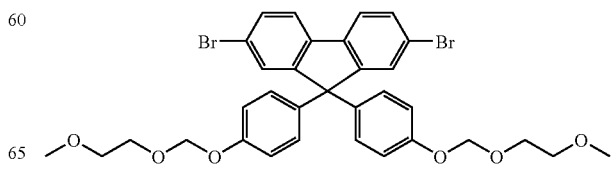

Melting point: 94-96° C. $^1$H-NMR (CDCl$_3$): δ=7.42-7.57 (m, 6H), 7.06 (d, 4H, J=8.8 Hz), 6.92 (d, 4H, J=8.8 Hz), 5.23 (s, 4H), 3.77-3.82 (m, 4H), 3.51-3.56 (m, 4H), 3.35 (s, 6H) $^{13}$C-NMR (CDCl$_3$): δ=156.2, 153.4, 137.8, 137.6, 130.8, 129.2, 129.0, 121.7, 121.5, 116.1, 93.4, 71.6, 67.7, 64.4, 59.0

Next, 3 g (4.4 mmol) of 2,7-dibromo-9,9'-bis[4-(2-methoxyethoxymethoxy)phenyl]-9H-fluorene, 1.5 g (9.2 mmol) of diphenylamine, 1.01 g (10.6 mmol) of sodium tert-butoxide and 20 ml of xylene were placed in a 100 ml eggplant type flask equipped with a reflux condenser under nitrogen atmosphere. Thereafter, 4 mg of palladium acetate and 10 mg of tri-tert-butylphosphine were added, the temperature was risen to 120° C., and the resulting mixture was stirred at the same temperature for 3 hours, and then cooled to room temperature. 30 ml of water was added to separate an organic phase, followed by condensation. As a result, 2,7-bis(diphenylamino)-9,9'-bis[4-(2-methoxyethoxy-methoxy)phenyl]-9H-fluorine (intermediate B) was isolated in an amount of 2.8 g (yield=75%). Identification was conducted with $^1$H-NMR and $^{13}$C-NMR.

Intermediate B

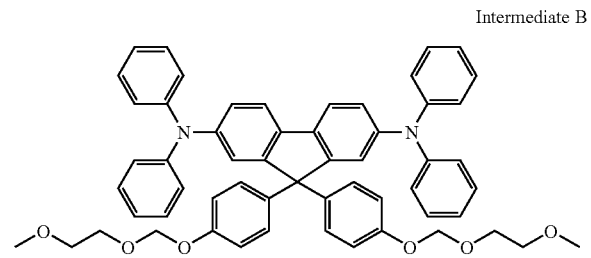

$^1$H-NMR (CDCl$_3$): δ=6.81-7.45 (m, 34H), 5.22 (s, 4H), 3.78-3.83 (m, 4H), 3.52-3.57 (m, 4H), 3.36 (s, 6H) $^{13}$C-NMR (CDCl$_3$): δ=155.8, 152.5, 147.6, 146.6, 139.0, 129.2, 129.0, 123.9, 123.3, 122.5, 121.8, 120.0, 115.6, 93.5, 71.6, 67.6, 64.0, 59.0

5 ml (30 mmol) of a 6N-hydrochloric acid aqueous solution was added to a reaction solution obtained by dissolving the compound obtained above in 20 ml of dichloromethane, reaction was conducted at room temperature for 5 hours, and water was added to separate an organic phase. The organic phase obtained was stirred at room temperature with addition of 1.03 g (13.0 mmol) of pyridine and 3.1 g (9.9 mmol) of trifluoromethanesulfonic anhydride. Water was added to separate and concentrate the organic phase, thereby isolating the desired 2,7-bis(diphenylamino)-9,9'-bis[4-(trifluoromethanesulfonyl-oxy)phenyl]-9H-fluorene (intermediate C). It was confirmed to be the desired product by FDMS.

Intermediate C

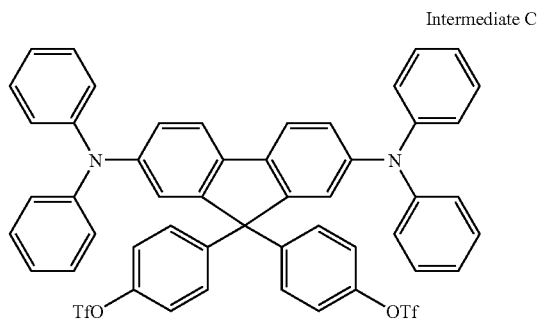

FDMS: 948

Synthesis Example 2

2.0 g (2.9 mmol) of 2,7-dibromo-9,9'-bis[4-(2-methoxyethoxymethoxy)phenyl]-9H-fluorene obtained in Synthesis Example 1, 1.70 g (5.9 mmol) of triphenylamineboronic acid, 9.4 g of 20% sodium carbonate, 10mg of tetrakis(triphenylphosphine)palladium and 15 ml of THF were placed in a 100 ml eggplant type flask equipped with a reflux condenser, and refluxed under heating for 5 hours. After stirring for a given period of time, the reaction solution was cooled to separate an organic layer. The organic layer was dried with anhydrous magnesium sulfate and then concentrated to isolate 2,7-bis(4-diphenylaminophenyl)-9,9'-bis[4-(2-methoxyethoxymethoxy)-phenyl]-9H-fluorene (intermediate D) in an amount of 2.37 g as a pale yellow powder. Identification was conducted with $^1$H-NMR and $^{13}$C-NMR.

Intermediate D

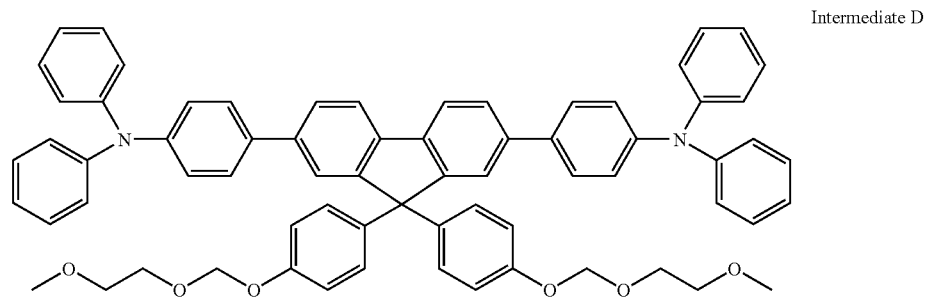

¹H-NMR (CDCl₃): δ=7.77 (d, 2H), 7.54-7.58 (m, 4H), 7.44 (d, 4H, J=8.8 Hz), 6.97-7.29 (m, 28H), 6.90 (d, 4H, J=8.8 Hz), 5.20 (s, 4H), 3.76-3.80 (m, 4H), 3.49-3.54 (m, 4H), 3.33 (s, 6H) ¹³C-NMR (CDCl₃): δ=155.9, 152.5, 147.5, 147.0, 139.9, 139.2, 138.4, 135.1, 129.2, 127.7, 126.0, 124.3, 124.2, 123.8, 122.8, 120.3, 115.9, 93.4, 71.6, 67.6, 64.4, 59.0

The compound obtained was treated with 6N hydrochloric acid aqueous solution and trifluoromethanesulfonic acid anhydride in the same manner as in Synthesis Example 1 to isolate 2,7-bis(4-diphenyl-aminophenyl)-9,9'-bis[4-(trifluoromethanesulfonyloxy)-phenyl]-9H-fluorene (intermediate E). It was confirmed to be the desired product by FDMS.

phino)ferrocene palladium, 0.991 g of sodium acetate and 20 ml of DMF were placed in a 100 ml eggplant type flask under nitrogen stream, and stirred under heating at 80° C. overnight. After cooling, the mixture was extracted with toluene, and an organic phase obtained was washed with 20 ml of water two times. The organic phase was dried with anhydrous magnesium sulfate, and after concentration, 1.1 g of 2,7-di(4,4,5,5-tetramethyl-1,3,2-dioxaborolan-2-yl)-9,9'-bis(4-methoxymethyloxyphenyl)-9H-fluorene (intermediate F) was synthesized. Identification was conducted with FDMS, ¹H-NMR and ¹³C-NMR, and it was confirmed to be the desired product.

Intermediate E

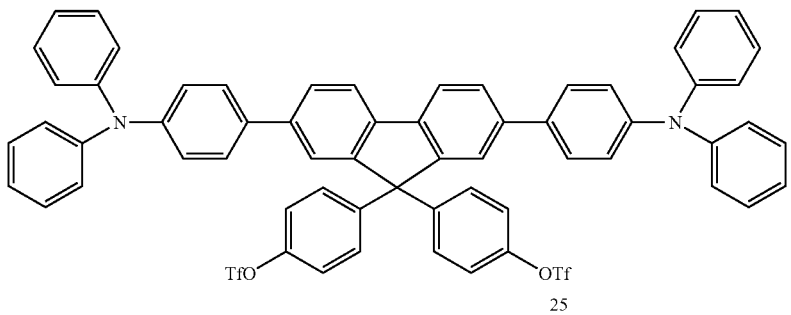

FDMS: 1100

Synthesis Example 3

2,7-bis(diphenylamino)-9,9'-bis[4-(trifluoromethane-sulfonyloxy)phenyl]-9H-fluorene (intermediate C) was isolated according to Synthesis Example 1, except for changing 2-methoxyethoxymethyl chloride to chloromethyl methyl ether. Identification of the intermediates obtained in each reaction was conducted with ¹H-NMR and ¹³C-NMR.

(1) 2,7-dibromo-9,9'-bis(4-methoxymethyloxyphenyl)-9H-fluorene

¹H-NMR (CDCl₃): δ=7.44-7.59 (m, 6H), 7.06 (d, 4H, H=8.8 Hz), 6.91 (d, 4H, J=8.8 Hz), 5.14 (s, 4H), 3.46 (s, 6H) ¹³C-NMR (CDCl₃): δ=156.2, 153.4, 137.8, 137.6, 130.8, 129.3, 129.0, 121.8, 121.5, 116.1, 94.3, 64.5, 56.1

(2) 2,7-bis(diphenylamino)-9,9'-bis(4-methoxymethyloxy-phenyl)-9H-fluorene

¹H-NMR (THF-d₈): δ=7.57 (d, 2H, J=8.2 Hz), 6.78-7.22 (m, 32H), 5.09 (s, 4H), 3.38 (s, 6H) ¹³C-NMR (THF-d₈): δ=156.9, 153.6, 148.5, 147.5, 139.5, 135.4, 129.7, 124.6, 123.8, 123.3, 122.4, 120.8, 116.2, 95.0, 64.9, 55.8

(3) 2,7-bis(diphenylamino)-9,9'-bis(4-hydroxyphenyl)-9H-fluorene

¹H-NMR (THF-d₈): δ=8.07 (br s, 2H), 7.55 (d, 2H, J=8.2 Hz), 6.84-7.18 (m, 24H), 6.52 (d, 4H, J=8.8 Hz) ¹³C-NMR (THF-d₈): δ=157.1, 154.4, 148.7, 127.5, 137.2, 135.7, 129.9, 129.8, 124.7, 123.9, 123.3, 122.9, 120.8, 115.4, 64.9

Synthesis Example 4

Synthesis of 2,7-di(4,4,5,5-tetramethyl-1,3,2-dioxaborolan-2-yl)-9,9'-bis(4-methoxymethyloxyphenyl)-9H-fluorene 1 g (1.68 mmol) of 2,7-dibromo-9,9'-bis(4-methoxy-methyloxyphenyl)-9H-fluorene, 0.94 g (3.70 mmol) of bis(pinacolato)diboron, 36.9 mmg of dichlorobis-(diphenylphos- Intermediate F

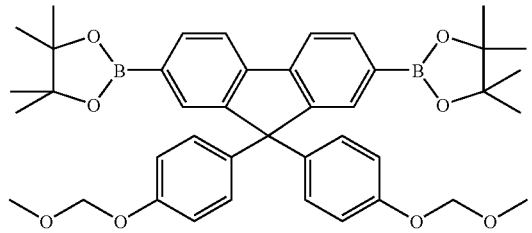

FDMS: 690 ¹H-NMR (THF-d₈): δ=7.76-7.84 (m, 6H), 7.07 (d, 4H, J=8.8 Hz), 6.85 (d, 4H, J=8.8 Hz), 5.08 (s, 4H), 3.37 (s, 6H), 1.29 (s, 24H) ¹³C-NMR (THF-d₈): δ=157.20, 152.57, 143.50, 139.73, 134.84, 132.85, 129.88, 120.45, 116.46, 95.12, 84.36, 65.18, 55.92, 25.28

Example 1

Synthesis of Compound 1

1.0 g (1.1 mmol) of the intermediate C obtained in Synthesis Example 1, 0.13 g (1.1 mmol) of phenylboronic acid, 5 g of 20% sodium carbonate, 20 mg of tetrakis(triphenylphosphine)palladium and 20 ml of THF were placed in a 50 ml eggplant type flask, and reacted under reflux for 2 hours. After cooling the reaction solution to room temperature, an organic layer as an upper layer was separated and concentrated, and the concentrated solution obtained was subjected to silica gel chromatography to isolate the desired product. It was confirmed to be the desired product by FDMS and ¹³C-NMR. The compound obtained was an amorphous compound having no melting point and having a glass transition temperature of 135° C.

FDMS: 804 ¹³C-NMR (CDCl₃): δ=153.1, 148.7, 147.8, 145.7, 141.6, 140.3, 135.7, 129.9, 129.4, 127.8, 127.5, 127.4, 124.9, 124.1, 123.5, 122.7, 121.1, 65.7

Compound (1)

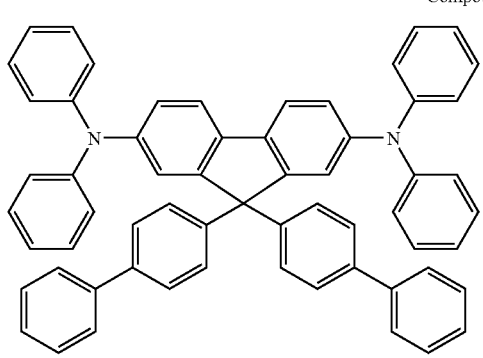

Example 2

Synthesis of Compound 23

1.2 g (1.1 mmol) of the intermediate E obtained in Synthesis Example 1, 0.13 g (1.1 mmol) of phenylboronic acid, 5 g of 20% sodium carbonate, 20 mg of tetrakis(triphenylphosphine)palladium and 20 ml of THF were placed in a 50 ml eggplant type flask, and reacted under reflux for 2 hours. After cooling the reaction solution to room temperature, an organic layer as an upper layer was separated and concentrated, and the concentrated solution obtained was subjected to silica gel chromatography to isolate the desired product. It was confirmed to be the desired product by FDMS. The compound obtained was an amorphous compound having a glass transition temperature of 207° C.

FDMS: 956

Compound (23)

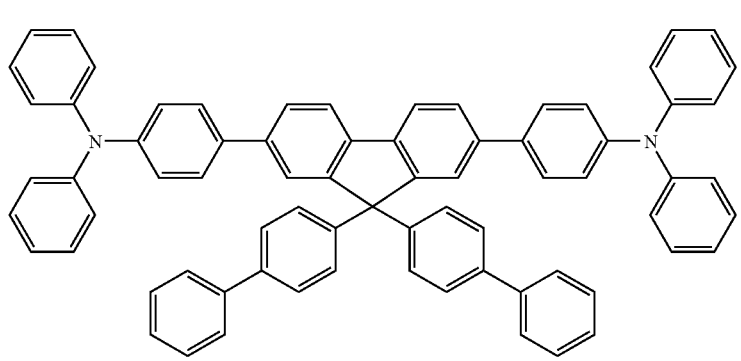

Example 3

Synthesis of Compound 3

The same procedures as in Example 1 were followed, except for changing phenylboronic acid to biphenylboronic acid, and compound 3 was isolated. Identification of the compound was conducted by FDMS.

FDMS: 956

Compound (3)

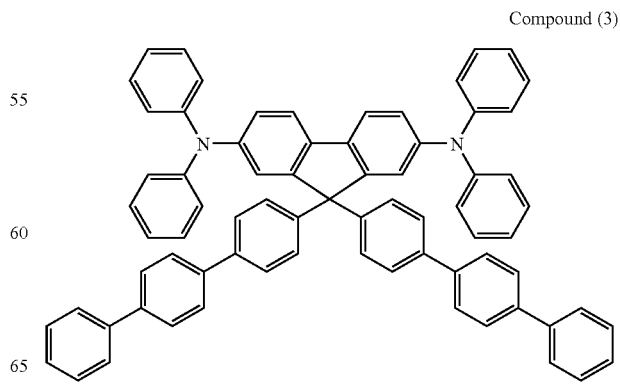

Example 4

Synthesis of Compound 4

The same procedures as in Example 1 were followed, except for changing phenylboronic acid to terphenylboronic acid, and compound 4 was isolated. Identification of the compound was conducted by FDMS.
FDMS: 1108

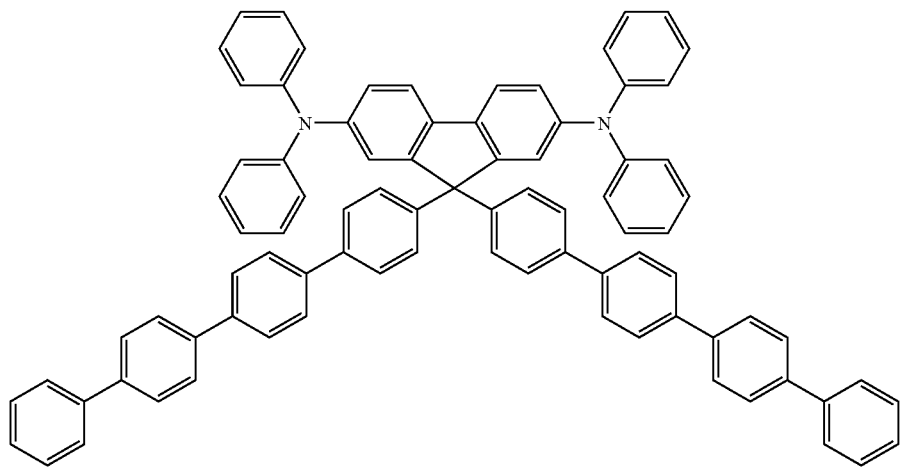

Compound (4)

Example 5

Synthesis of Compound 5

The same procedures as in Example 1 were followed, except for changing phenylboronic acid to 9-anthrylboronic acid, and compound 5 was isolated. Identification of the compound was conducted by FDMS.
FDMS: 1004

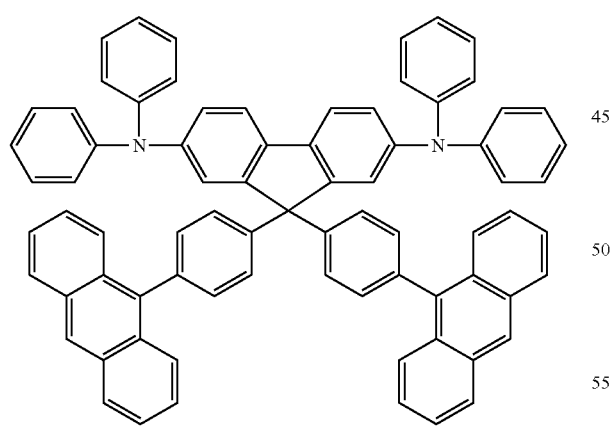

Compound (5)

Examples 6-12

Syntheses of Compounds 9, 10, 12, 15, 21, 22 and 78

Compounds 9, 10, 12, 15, 21, 22 and 78 each was synthesized according to Synthesis Example 1 and Example 1. Glass transition temperature of each compound is shown in Table 12.

TABLE 12
| | Example 6 | Example 7 |
|---|---|---|
| Compound | 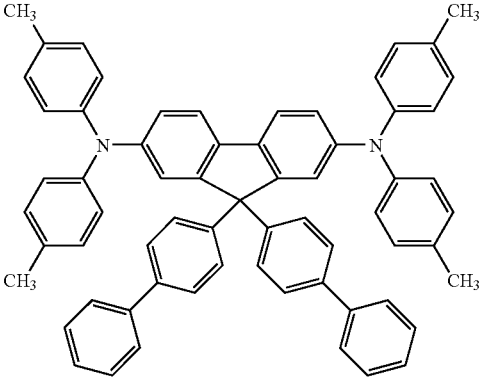<br>Compound 9 | 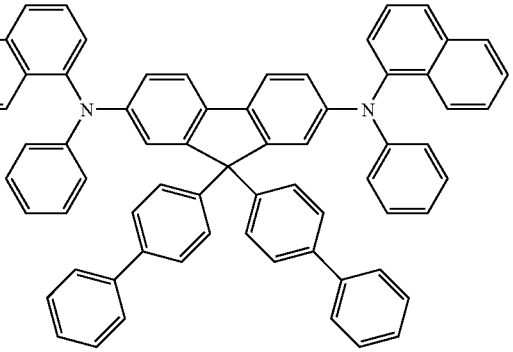<br>Compound 10 |
| Glass transition temperature | 136° C. | 139° C. |
| | Example 8 | Example 9 |
|---|---|---|
| Compound | 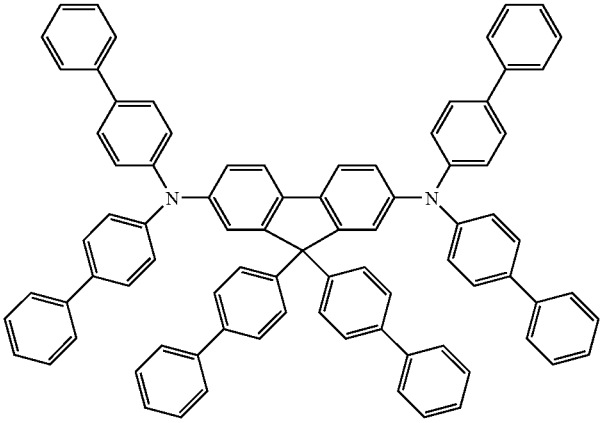<br>Compound 12 | 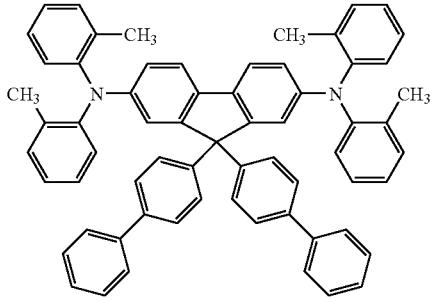<br>Compound 21 |
| Glass transition temperature | 157° C. | 139° C. |
| | Example 10 | Example 11 |
|---|---|---|
| Compound | 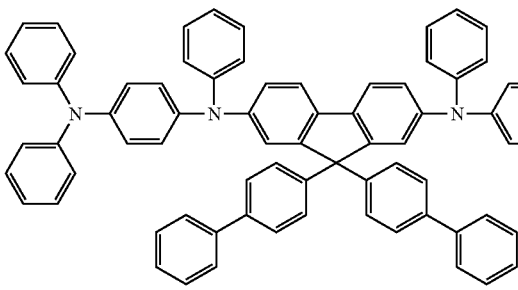<br>Compound 22 | 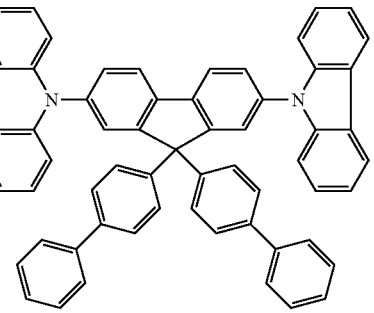<br>Compound 78 |
| Glass transition temperature | 151° C. | 178° C. |

TABLE 12-continued

Example 12

| Compound | 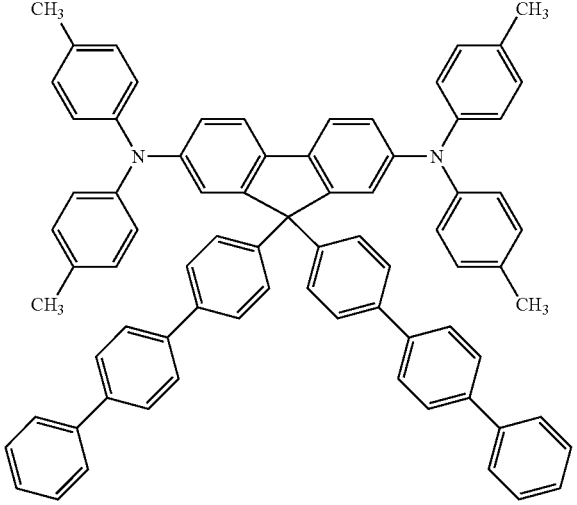 |
|---|---|
| | Compound 15 |
| Glass transition temperature | 154° C. |

Example 13

Synthesis of Compound 23

1 g (1.45 mmol) of 2,7-di(4,4,5,5-tetramethyl-1,3,2-dioxaborolan-2-yl)-9,9'-bis(4-methoxymethyloxyphenyl)-9H-fluorene (intermediate F) obtained in Synthesis Example 4, 0.94 g (2.90 mmol) of bromotriphenylamine, 4 g of 20% sodium carbonate, 20 mg of tetrakis(triphenylphosphine)palladium and 20 ml of THF were placed in a 50 ml eggplant type flask, and reacted under reflux for 8 hours. After cooling the reaction solution to room temperature, an organic layer as an upper layer was separated and concentrated, and the concentrated solution obtained was subjected to silica gel chromatography to isolate the desired product. It was confirmed to be 2,7-bis(4-diphenylaminophenyl)-9,9'-bis(4-methoxymethyloxyphenyl)-9H-fluorene (intermediate G) by FDMS.

Hydrochloric acid treatment, trifluoromethane-sulfonylation and coupling treatment were conducted according to Synthesis Example 1 and Example 1 to synthesize compound 23. Identification was conducted by FDMS.

FDMS: 956

Example 14

Synthesis of Compound 40

The same procedures as in Example 13 were followed, except for changing bromotriphenylamine to 4'-di(p-tolyl)amino-4-bromobiphenyl, and 2,7-bis[4'-di(p-tolylamino)biphenyl-4-yl]-9,9'-bis(4-methoxymethyloxy-phenyl)-9H-fluorene was obtained. The same treatment as in Example 13 was conducted to obtain compound 40. Identification was conducted with FDMS.

FDMS: 1164

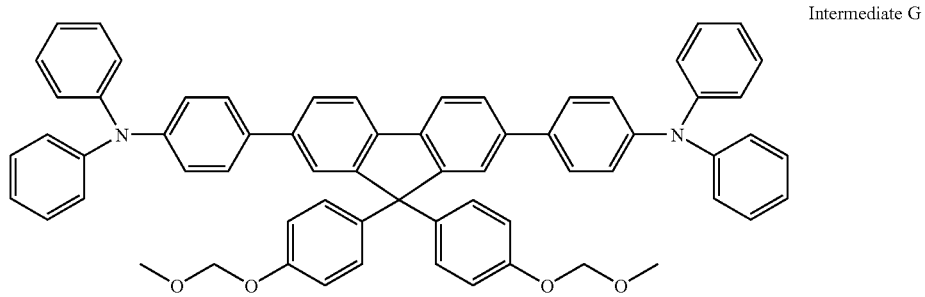

Intermediate G

FDMS: 924

Example 15

Synthesis of Compound 51

The same procedures as in Example 13 were followed, except for changing bromotriphenylamine to 7-di(p-tolyl)amino-9,9'-dimethyl-2-bromofluorene, and 2,7-bis[7-di(p-tolyl)amino-9,9'-dimethylfluoren-2-yl)-9,9'-bis(4-methoxymethyloxyphenyl)-9H-fluorene was obtained. The same treatment as in Example 13 was conducted to obtain compound 51. Identification was conducted with FDMS.
FDMS: 1244

Example 16

Synthesis of Compound 62

The same procedures as in Example 13 were followed, except for changing bromotriphenylamine to 7-[(4-di-p-tolylamino)phenyl]-4-bromo-2,1,3-benzothiadiazole, and 2,7-bis(7-(4-di-p-tolyamino)phenyl-2,1,3-benzothiadiazol-4-yl)-9,9'-bis(4-methoxymethyloxyphenyl)-9H-fluorene was obtained. The same treatment as in Example 13 was conducted to obtain compound 62. Identification was conducted with FDMS.
FDMS: 1280

Example 17

Synthesis of Compound 34

5.18 g (7.50 mmol) of 2,7-di(4,4,5,5-tetramethyl-1,3,2-dioxaborolan-2-yl)-9,9'-bis(4-methoxymethyloxy-phenyl)-9H-fluorene) (intermediate F) obtained in Synthesis Example 4, 5.70 g (14.3 mmol) of 4-bromo-4'-(diphenylamino)biphenyl, 30 g of 20% sodium carbonate, 233 mg of dichlorobis(diphenylaminophenylferrocene)palladium and 60 ml of THF were placed in a 50 ml eggplant type flask, and reacted under reflux overnight. After cooling the reaction solution to room temperature, an organic layer as an upper layer was separated and concentrated, and the concentrated solution obtained was subjected to silica gel chromatography to isolate the desired product. It was confirmed to be 2,7-bis(4-diphenylaminobiphenyl)-9,9'-bis(4-methoxymethyloxyphenyl)-9H-fluorene (intermediate H) by $^{13}$C-NMR and FDMS.

$^{13}$C-NMR (THF-$d_8$): 157.14, 153.66, 148.47, 148.07, 140.84, 140.16, 140.09, 139.83, 139.72, 135.29, 129.87, 129.81, 128.09, 127.89, 127.32, 126.90, 124.98, 124.56, 123.59, 121.26, 116.47, 94.99, 65.36, 55.82 FDMS: 1076

6N hydrochloric acid aqueous solution was added dropwise to 60 ml of THF solution of the intermediate H obtained above at room temperature, and the resulting solution was then stirred at 40° C. overnight. After completion of the reaction, the solution was extracted by adding 50 ml of toluene, and washed three times with 30 ml of water. An organic layer was dried with magnesium sulfate, and then concentrated. The concentrated solution obtained, 2.99 g (10.6 mmol) of trifluoromethanesulfonic acid anhydride, 3.82 g (48.3 mmol) of pyridine and 50 ml of toluene were charged, and after stirring at room temperature overnight, ordinary treatment methods were conducted to obtain the corresponding sulfonic acid ester. Finally, reaction was conducted with phenylboronic acid in the presence of tetrakis(triphenylphosphine)palladium catalyst to synthesize compound 34. Identification was conducted with FDMS, $^1$H-NMR and $^{13}$C-NMR. The glass transition temperature was 183° C.

An element of the compound 34 having a film thickness of 1.2 μm was prepared on ITO electrode by vacuum deposition. Mobility was measured by Time of Flight method (TOF-301, a product of Optel Co.). As a result, it showed bipolar properties of hole mobility=1×10$^{-3}$ cm$^2$/V·s and electron mobility=4×10$^{-4}$ cm$^2$/V·s. From this fact, it was confirmed that the element can be used as a luminescent material.

FDMS: 1108 $^1$H-NMR (THF-$d_8$): 7.99 (d, 2H, J=8 Hz), 6.97-7.87 (m, 48H) $^{13}$C-NMR (THF-$d_8$): 153.0, 148.47, 148.07, 145.78, 141.39, 141.02, 140.31, 140.18, 140.09, 139.92, 135.27, 129.81, 129.38, 129.23, 128.08, 127.89, 127.67, 127.51, 127.34, 127.12, 125.16, 124.98, 124.56, 123.52, 121.34, 66.13

Example 18

Synthesis of Compound 37

The same procedures as in Example 17 were followed, except for changing phenylboronic acid to 9-anthraceneboronic acid, to synthesize compound 37. Identification was conducted with FDMS.
FDMS: 1308

Example 19

Synthesis of Compound 38

The same procedures as in Example 17 were followed, except for changing phenylboronic acid to 10-phenyl-9-anthraceneboronic acid, to synthesize compound 38. Identification was conducted with FDMS.
FDMS: 1406

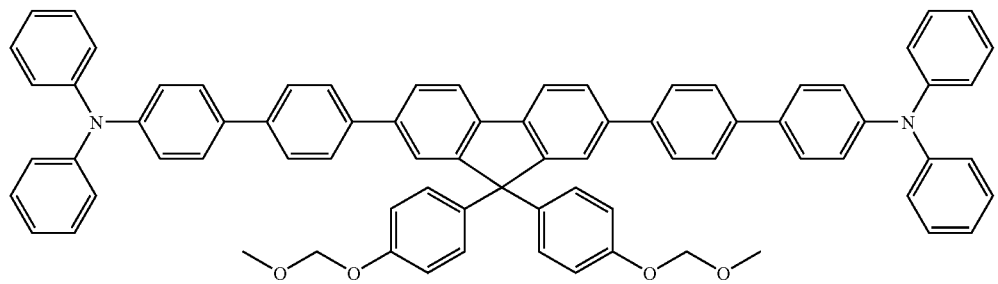

Intermediate H

Example 20

Synthesis of Compound 39

The same procedures as in Example 17 were followed, except for changing phenylboronic acid to 2-9,9'-dimethylfluoreneboronic acid, to synthesize compound 39. Identification was conducted with FDMS.
FDMS: 1340

Comparative Examples 1-3

Figure 2:
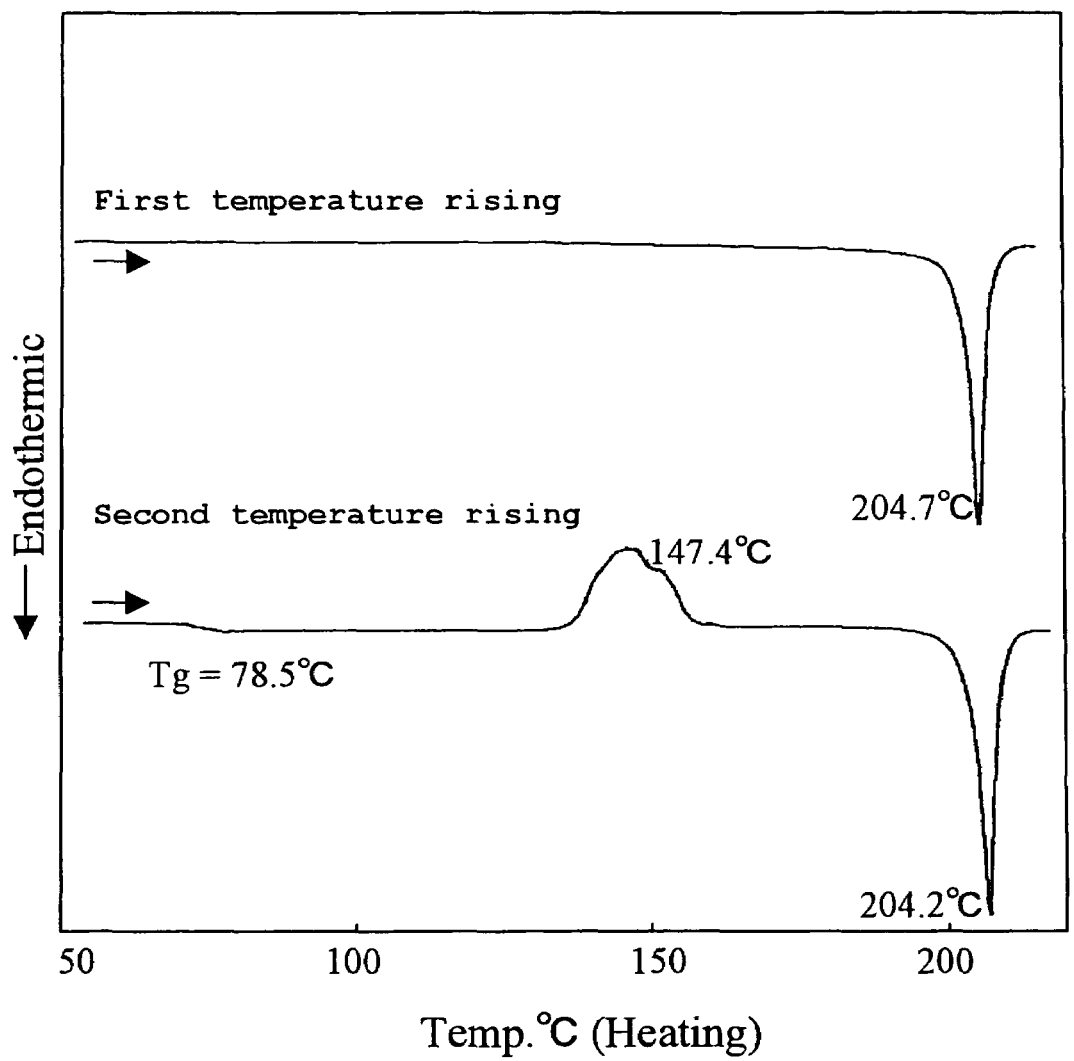
Figure 3:
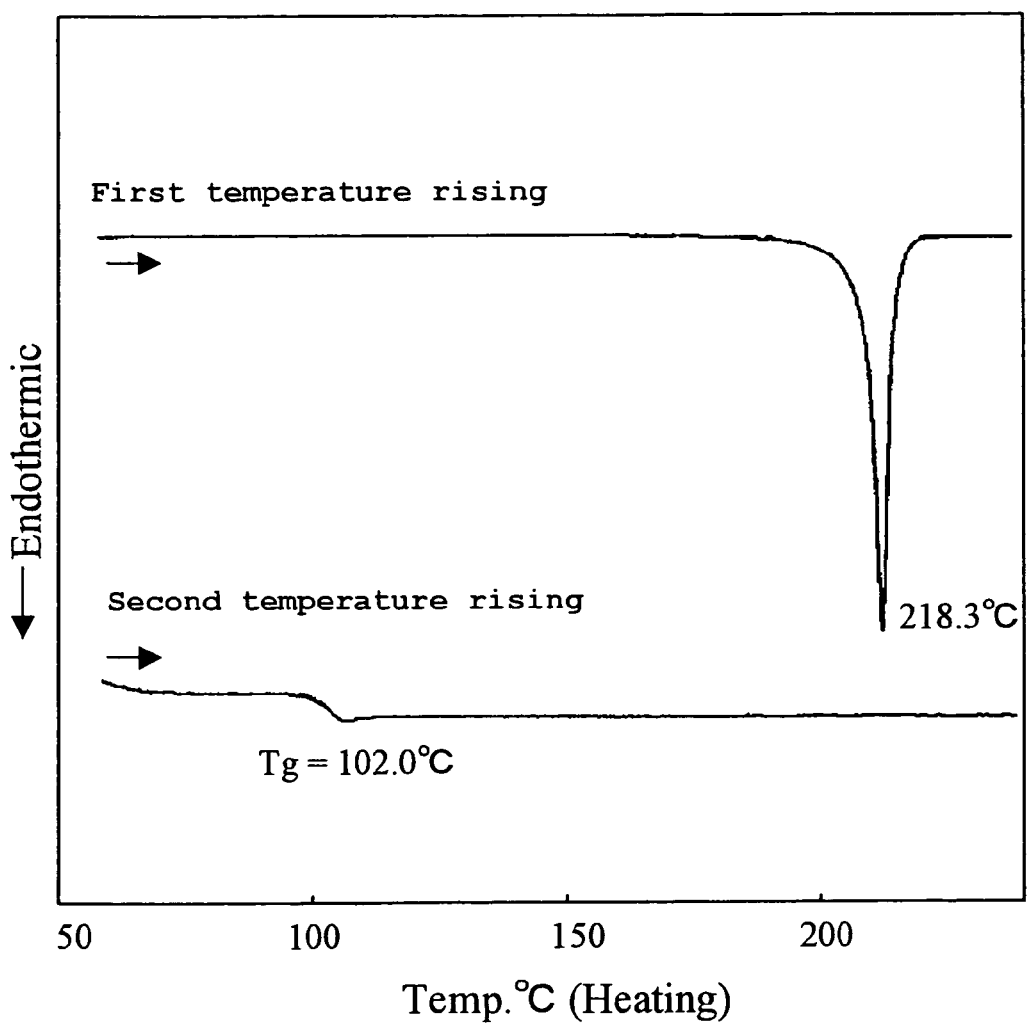
Figure 4:
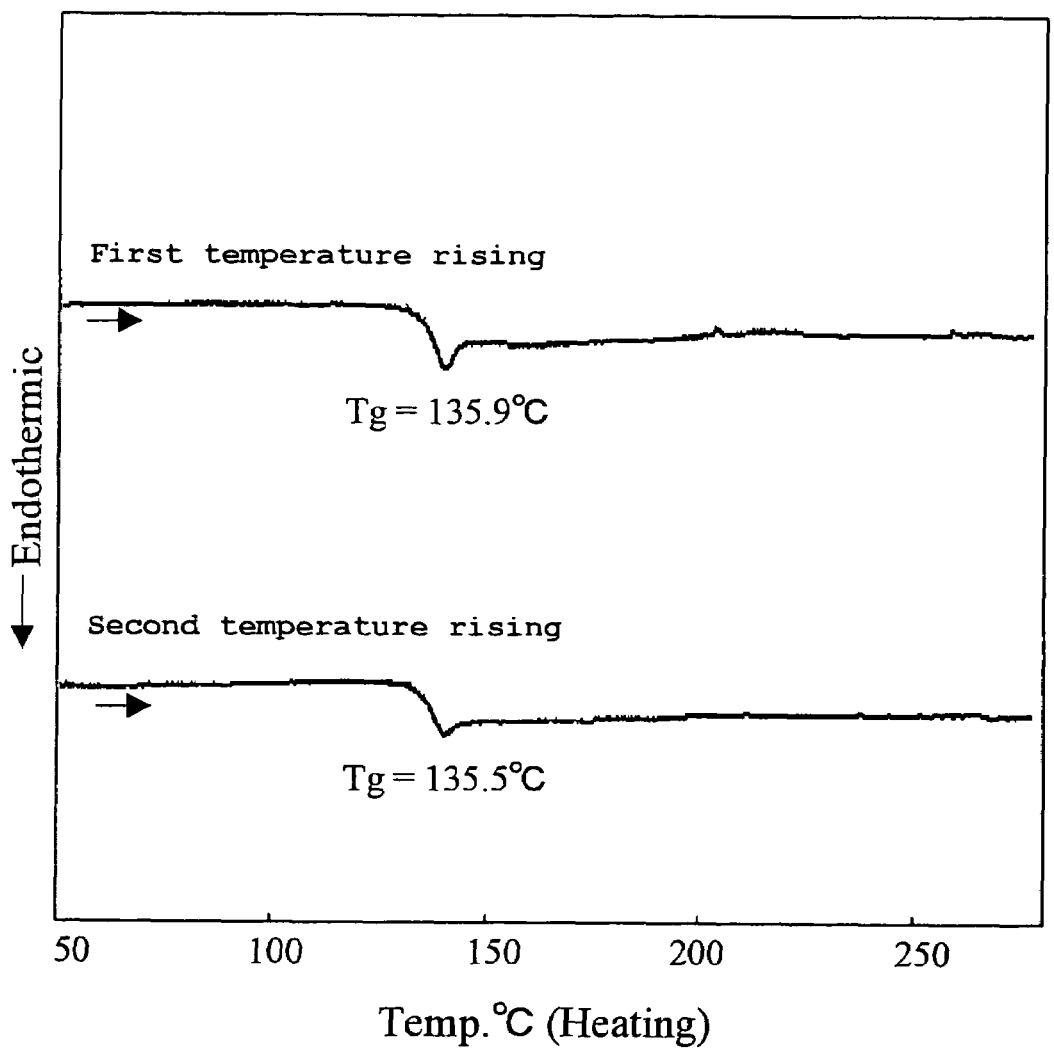

Compounds each having p-methoxyphenyl group, benzyl group or n-octyl group at 9,9'-positions of fluorene group in the compound 1 shown in Example 1 were synthesized according to reaction routes shown below, and the respective melting point and glass transition temperature were measured by a differential thermal analysis. The results are shown in Table 13 together with the melting point and glass transition temperature of the compound 1 shown in Example 1. The compounds of Comparative Examples 1-3 were crystalline compounds showing definite melting point, and the glass transition temperature was 110° C. or lower. On the other hand, the compound 1 was an amorphous material not showing definite melting point and having a glass transition temperature of 135° C. Further, differential thermal analysis charts of each compound are shown in FIGS. 1-4.

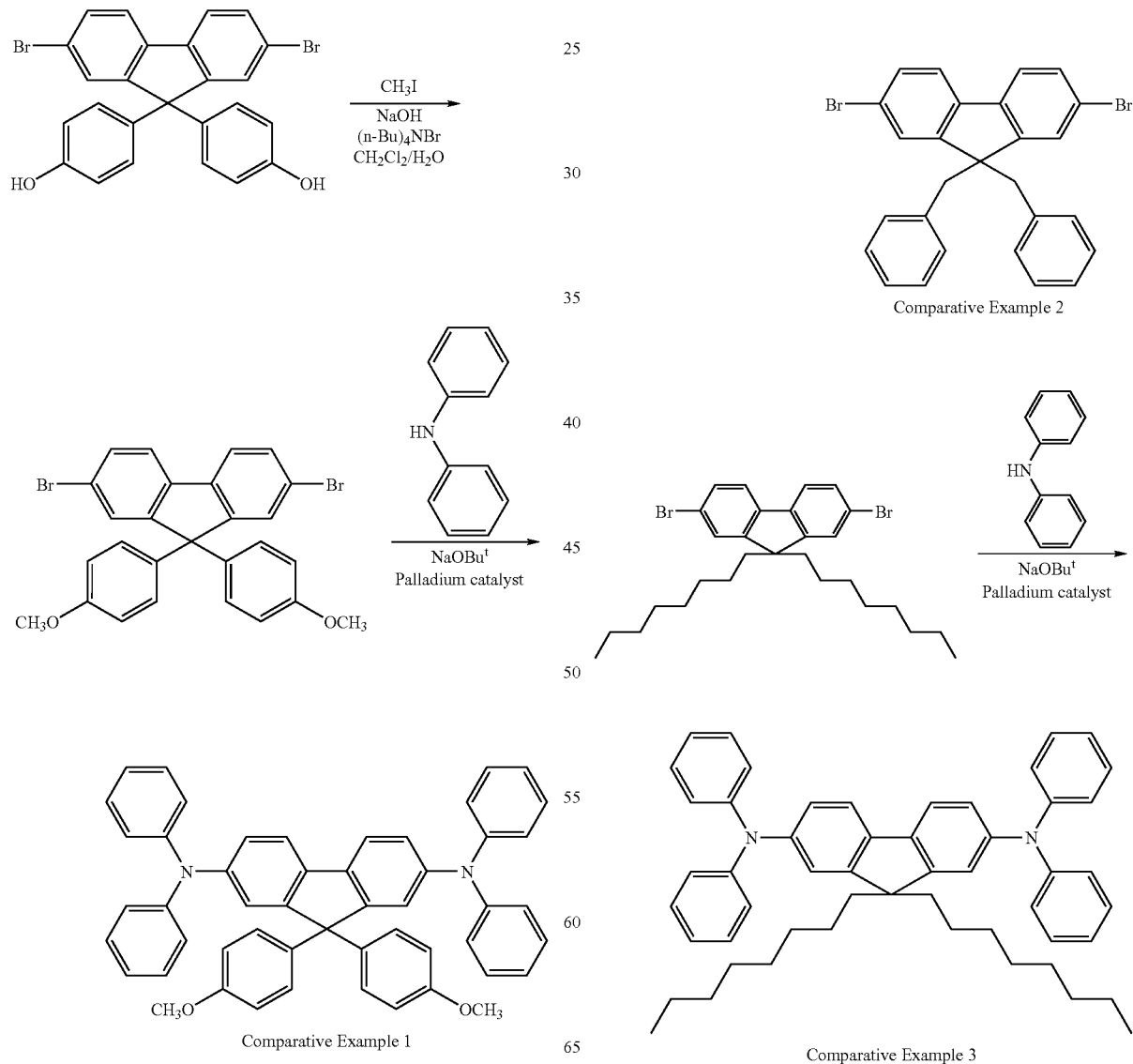

TABLE 13

| | Comparative Example 1 | Comparative Example 2 |
|---|---|---|
| Structure | (structure with CH₃O and OCH₃ substituents on fluorene spiro diaryl) | (structure with dibenzyl substituents on fluorene) |
| Melting point/° C. | 210-213 | 195-197 |
| Glass transition temperature/° C. | 102 | 78 |

| | Comparative Example 3 | Example 1 |
|---|---|---|
| Structure | (structure with dialkyl substituents on fluorene) | (structure with biphenyl substituents on fluorene) |
| Melting point/° C. | 101-102 | Not detected |
| Glass transition temperature/° C. | 18 | 135 |

Example 21

20 mg of each of the compound 1 obtained in Example 1 and the compounds obtained in Comparative Examples 1-3 was dissolved in 2 ml of toluene to prepare a 1% solution. A thin film was prepared on a quartz substrate by a spin coat method (revolution condition=1000 rpm (1 minute), vacuum heating condition=60° C. (1 hour) vacuum heating), and allowed to stand at room temperature (1 month) to examine white turbidity (or cohesion) of each thin film. As a result, white turbidity was not observed at all in the thin film of compound 1. On the other hand, the compounds of Comparative Examples 1-3 showed partially white turbidity.

Example 22

Using a glass substrate having formed thereon ITO electrode (anode), which had successively been subjected to acetone washing, ion exchanged water washing, isopropyl alcohol boiled solution washing and UV-ozone washing, compound 1 was deposited on the ITO anode up to a film thickness of 40 nm at a deposition rate of 4 angstroms/sec to form a hole transport layer. Next, tris(8-quinolinorato) aluminum was deposited on the compound 1 up to a film thickness of 50 nm at a deposition rate of 4 angstroms/sec to form an electron transport and luminescent layer. Next, magnesium and silver in an atomic ratio of 10:1 (=Mg:Ag) were co-deposited on the tris(8-quinolinorato) aluminum up to a film thickness of 150 nm to form a cathode. Thus, an organic electroluminescence device was formed. Each thin film was laminated by a vacuum deposition method at a degree of vacuum of $1.0 \times 10^{-5}$ Torr.

The organic EL device thus produced showed a luminance of 500 cd/m² at a current density of 8 mA/cm² and a voltage of 7 V. This device was stored at 90° C. for 100 hours under vacuum, and current-luminance characteristics were measured. As a result, change was not substantially recognized.

Comparative Example 4

An organic electroluminescence device was produced in the same manner as in Example 22, except that the compounds shown in Comparative Examples 1-3 were used as a hole transport layer in place of the compound 1 synthesized in Example 1. This device was stored at 90° C. for 100 hours under vacuum, and current-luminance characteristics were measured. As a result, deterioration of luminance was fast as compared with the device of Example 22 to the same electric current.

While the invention has been described in detail and with reference to the specific embodiments thereof, it will be apparent to one skilled in the art that various changes or modifications can be made therein without departing from the spirit and scope thereof.

This application is based on Japanese Patent Application (Application No. 2004-7824) filed Jan. 15, 2004 and Japanese Patent Application (Application No. 2004-10698) filed Mar. 31, 2004, the contents thereof being hereby incorporated by reference.

INDUSTRIAL APPLICABILITY

An amine compound having a fluorene group as a mother nucleus, represented by the general formula (1) according to the present invention has high Tg, and many of those have an amorphous structure. Therefore, the amine compound is excellent in stability and durability as compared with the conventionally reported materials, and can be utilized as hole transport materials, luminescent materials or the like of organic EL devices, electrophotographic receptors or the like.

The invention claimed is:

1. An amine compound represented by the general formula (1):

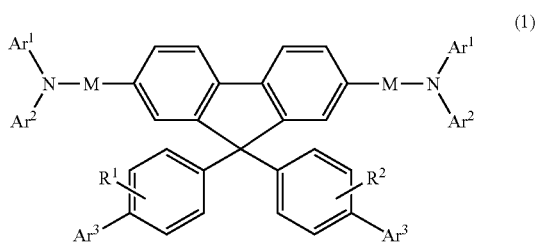

(1)

wherein $R^1$ and $R^2$ each independently represents hydrogen atom, a linear, branched or cyclic alkyl group or alkoxy group, an aryl group, an aryloxy group or a halogen atom; $Ar^1$ and $Ar^2$ each independently represents a substituted or unsubstituted aryl group or heteroaryl group, and may form a nitrogen-containing heterocyclic ring together with the nitrogen atom bonded thereto; and $Ar^3$ each independently represents a substituted or unsubstituted phenyl group, naphthyl group, biphenylyl group, terphenylyl group, anthryl group, fluorenyl group or pyridyl group (except for amino-substituted groups); and M represents a single bond, an arylene group or a heteroarylene group.

2. The amine compound as claimed in claim 1, characterized in that at least one of $Ar^1$ and $Ar^2$ is a substituted or unsubstituted condensed ring aromatic group.

3. The amine compound as claimed in claim 2, characterized in that the condensed ring aromatic group is 1-naphthyl group, 9-phenanthryl group, pyrenyl group or 2-fluorenyl group.

4. The amine compound as claimed in claim 1, characterized in that in the general formula (1), $Ar^1$ and $Ar^2$ each independently is phenyl group, 4-methylphenyl group or 4-biphenylyl group.

5. The amine compound as claimed in claim 1, characterized in that in the general formula (1), $Ar^3$ is phenyl group, 3,5-diphenylphenyl group, 1-naphthyl group, 4-biphenylyl group, 4-terphenylyl group, 9-anthryl group, 10-phenyl-9-anthryl group or 10-(3,5-diphenylphenyl)-9-anthryl group.

6. The amine compound as claimed in claim 1, characterized in that in the general formula (1), M is phenylene group, 1,4-naphthalenediyl group, 2,6-naphthalenediyl group, 4,4'-biphenyldiyl group, 4,4'-terphenyldiyl group, 9,10-anthracenediyl group or 2,7-9,9'-dialkylfluorenediyl group.

7. The amine compound as claimed in claim 1, characterized in that in the general formula (1), M is the following general formulae (2a)-(2f):

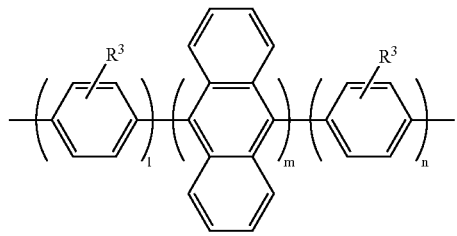

(2a)

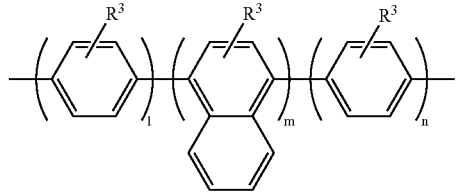

(2b)

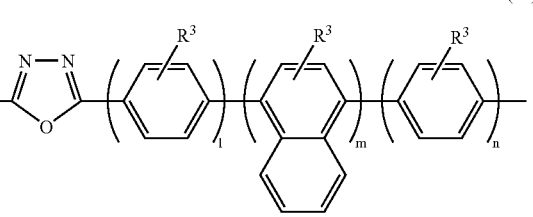

(2c)

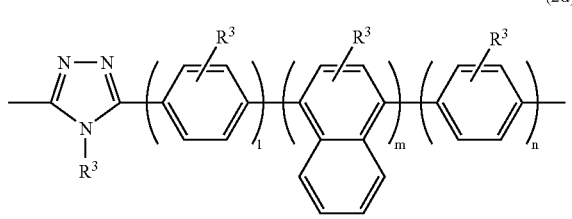

(2d)

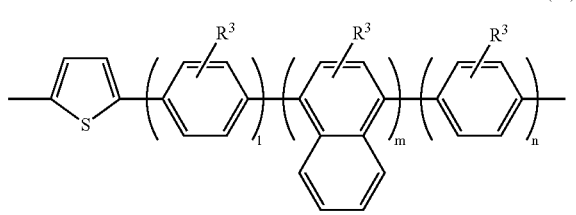

(2e)

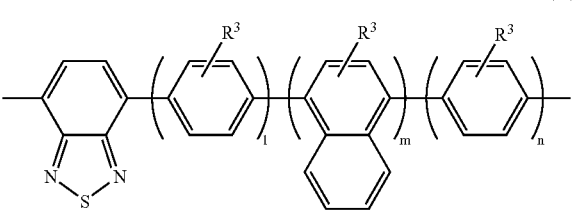

(2f)

wherein R³ represents hydrogen atom, an alkyl group or alkoxyl group having from 1 to 18 carbon atoms, or an aryl group having from 6 to 12 carbon atoms; and l, m and n represent a positive integer satisfying $1 \leqq l+m+n \leqq 4$.

8. The amine compound as claimed in claim 1, characterized in that R¹ and R² are hydrogen atom.

9. The amine compound as claimed in claim 1, characterized in that R¹ and R² are hydrogen atom, and M is a single bond, and it is represented by the following general formula (3):

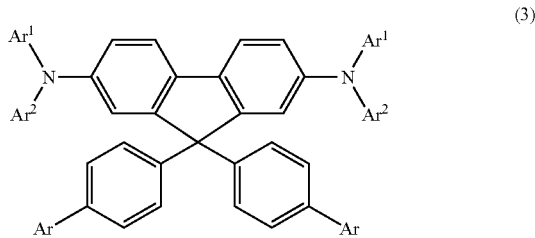

(3)

wherein Ar¹ and Ar² each independently represents substituted or unsubstituted aryl group or heteroaryl group, and may form a nitrogen-containing heterocyclic ring together with the nitrogen atom bonded thereto; and Ar represents phenyl group, 4-methylphenyl group, 3,5-diphenylphenyl group, 1-naphthyl group, 4-biphenylyl group, 4-terphenylyl group, 9-anthryl group, 10-phenyl-9-anthryl group or 10-(3, 5-diphenylphenyl)-9-anthryl group.

10. The amine compound as claimed in claim 9, characterized in that Ar¹ and Ar² each independently is phenyl group, 4-methylphenyl group, 4-biphenylyl group or 1-naphthyl group.

11. The amine compound as claimed in claim 1, characterized by having an amorphous structure.

12. The amine compound as claimed in claim 9, characterized by having an amorphous structure.

13. A process of producing the amine compound as claimed in claim 1, characterized by reacting fluorene derivatives represented by the following general formula (4) and arylboronic acid represented by the following general formula (5) in the presence of a palladium catalyst

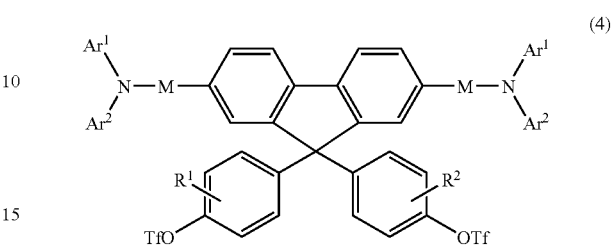

(4)

wherein R¹ and R² each independently represents hydrogen atom, a linear, branched or cyclic alkyl group or alkoxy group, an aryl group, an aryloxy group or a halogen atom; Ar¹ and Ar² each independently represents a substituted or unsubstituted aryl group or heteroaryl group, and may form a nitrogen-containing heterocyclic ring together with the nitrogen atom bonded thereto; M represents a single bond, an arylene group or a heteroarylene group; and Tf represents trifluoromethanesulfonyl group, $$Ar^3—B(OH)_2 \quad (5)$$

wherein Ar³ represents a substituted or unsubstituted phenyl group, naphthyl group, biphenylyl group, terphenylyl group, anthryl group, fluorenyl group or pyridyl group (except for amino-substituted groups).

14. An organic electroluminescence device, characterized by using the amine compound as claimed in claim 1 in either of a luminescent layer, a hole transport layer or a hole injection layer.

\* \* \* \* \*

UNITED STATES PATENT AND TRADEMARK OFFICE
CERTIFICATE OF CORRECTION

PATENT NO.         : 7,482,490 B2
APPLICATION NO. : 10/585945
DATED              : January 27, 2009
INVENTOR(S)        : Nishiyama et al.

It is certified that error appears in the above-identified patent and that said Letters Patent is hereby corrected as shown below:

On the title page, Item (30), the Foreign Application Priority Data has been omitted. Item (30) should read:

-- (30)      Foreign Application Priority Data

Jan. 15, 2004 (JP)..........................................2004-007824
Mar. 31, 2004 (JP)..........................................2004-106968 --

Signed and Sealed this

Twenty-fourth Day of March, 2009

JOHN DOLL
*Acting Director of the United States Patent and Trademark Office*